US010613615B2

(12) United States Patent
Niikura et al.

(10) Patent No.: US 10,613,615 B2
(45) Date of Patent: Apr. 7, 2020

(54) ELECTRONIC APPARATUS, INFORMATION PROCESSING SYSTEM, AND INFORMATION PROCESSING METHOD

(71) Applicant: SONY CORPORATION, Tokyo (JP)

(72) Inventors: Hideo Niikura, Tokyo (JP); Masakazu Yajima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 191 days.

(21) Appl. No.: 15/566,763

(22) PCT Filed: May 16, 2016

(86) PCT No.: PCT/JP2016/002380
§ 371 (c)(1),
(2) Date: Oct. 16, 2017

(87) PCT Pub. No.: WO2016/203702
PCT Pub. Date: Dec. 22, 2016

(65) Prior Publication Data
US 2018/0136712 A1 May 17, 2018

(30) Foreign Application Priority Data
Jun. 18, 2015 (JP) ................................. 2015-122932

(51) Int. Cl.
*G06F 1/32* (2019.01)
*G06F 1/3287* (2019.01)
(Continued)

(52) U.S. Cl.
CPC .............. *G06F 1/3287* (2013.01); *G06F 1/32* (2013.01); *H02J 7/0068* (2013.01); *H02J 7/34* (2013.01);
(Continued)

(58) Field of Classification Search
CPC ............................. G06F 1/3287; H04L 67/12
See application file for complete search history.

(56) References Cited

U.S. PATENT DOCUMENTS

2012/0068827 A1* 3/2012 Yi ............................ G01D 5/18
340/10.1
2013/0066594 A1* 3/2013 Ludlow .................. H02N 2/186
702/188
(Continued)

FOREIGN PATENT DOCUMENTS

CN          103100203 A    5/2013
JP          2013-105319 A  5/2013

OTHER PUBLICATIONS

International Search Report and Written Opinion of PCT Application No. PCT/JP2016/002380, dated Jun. 14, 2016, 09 pages of ISRWO.

*Primary Examiner* — Albert Wang
(74) *Attorney, Agent, or Firm* — Chip Law Group

(57) ABSTRACT

An electronic apparatus according to one embodiment of the present technology includes a sensor, a power storage element, and a communication module. The sensor generates charge in accordance with a surrounding environment. The power storage element accumulates the generated charge. The communication module includes an electric power supply unit and a communication processing unit. The electric power supply unit supplies electric power by generating electric power with energy in a surrounding environment. The communication processing unit is configured to be capable of being switched between a stand-by state and an operating state on the basis of the electric power supplied from the electric power supply unit and is configured to be capable of acquiring accumulation information of the charge from the power storage element and outputting the accumulation information in the operating state.

20 Claims, 28 Drawing Sheets

(51) Int. Cl.
*H04L 29/08* (2006.01)
*H02J 7/34* (2006.01)
*H02J 7/35* (2006.01)
*H02J 9/00* (2006.01)
*H02J 7/00* (2006.01)

(52) U.S. Cl.
CPC ................ *H02J 7/35* (2013.01); *H02J 9/005* (2013.01); *H04L 67/12* (2013.01)

(56) References Cited

U.S. PATENT DOCUMENTS

| | | |
|---|---|---|
| 2013/0124120 A1 | 5/2013 | Maruyama et al. |
| 2015/0257203 A1* | 9/2015 | Okada ................... G08C 15/00 370/338 |

* cited by examiner

ELECTRONIC APPARATUS, INFORMATION PROCESSING SYSTEM, AND INFORMATION PROCESSING METHOD

CROSS REFERENCE TO RELATED APPLICATIONS

This application is a U.S. National Phase of International Patent Application No. PCT/JP2016/002380 filed on May 16, 2016, which claims priority benefit of Japanese Patent Application No. JP 2015-122932 filed in the Japan Patent Office on Jun. 18, 2015. Each of the above-referenced applications is hereby incorporated herein by reference in its entirety.

TECHNICAL FIELD

The present technology relates to an electronic apparatus, an information processing system, and an information processing method that use an energy harvesting technology.

BACKGROUND ART

There is known a device capable of communicating with an external apparatus by using the technology of so-called energy harvesting that generates electric power on the basis of energy present in a surrounding environment, such as solar power generation and vibration power generation.

For example, Patent Literature 1 discloses a power generation device including a power generation unit that generates electric power on the basis of energy present in a surrounding environment. This power generation device has a communication function and is configured to be capable of transmitting power generation information to a host apparatus.

Meanwhile, since electric power generated by energy harvesting is minute, the technology that efficiently uses the minute electric power is anticipated.

For example, Patent Literature 2 discloses a power storage circuit including a first capacitance connected to an input terminal to which a minute current is input, an electric-field detection type switch whose on/off is controlled in accordance with a power storage voltage of the first capacitance, a second capacitance connected to the electric-field detection type switch, and an electronic circuit switch whose on/off is controlled in accordance with a power storage voltage of the second capacitance.

CITATION LIST

Patent Literature

Patent Literature 1: Japanese Patent Application Laid-open No. 2013-105319
Patent Literature 2: Japanese Patent Application Laid-open No. 2009-219266

DISCLOSURE OF INVENTION

Technical Problem

However, according to the technology described in Patent Literature 2, since the device is not activated until a power storage amount supplied by power generation becomes sufficient, information on the environment and the like in a stand-by state of the device cannot be acquired.

In view of the circumstances as described above, it is an object of the present technology to provide an electronic apparatus, an information processing method therefor, and an information processing system including an electronic apparatus, which are capable of achieving electric power saving and acquiring environment information in a stand-by state.

Solution to Problem

In order to achieve the object described above, an electronic apparatus according to one embodiment of the present technology includes a sensor, a power storage element, and a communication module.

The sensor generates charge in accordance with a surrounding environment.

The power storage element accumulates the generated charge.

The communication module includes an electric power supply unit and a communication processing unit.

The electric power supply unit supplies electric power by generating electric power with energy in a surrounding environment.

The communication processing unit is configured to be capable of being switched between a stand-by state and an operating state on the basis of the electric power supplied from the electric power supply unit and is configured to be capable of acquiring accumulation information of the charge from the power storage element and outputting the accumulation information in the operating state.

An information processing method for an electronic apparatus according to another embodiment of the present technology includes the steps of:
generating, by a sensor, charge in accordance with a surrounding environment;
accumulating, by a power storage element, the generated charge;
supplying, by an electric power supply unit of a communication module, electric power by generating electric power with energy in a surrounding environment;
switching a communication processing unit of the communication module between a stand-by state and an operating state on the basis of the electric power supplied from the electric power supply unit;
acquiring, by the communication processing unit, accumulation information of the charge from the power storage element and outputting the accumulation information in the operating state.

An information processing system according to still another embodiment of the present technology includes an electronic apparatus and a processing apparatus.

The electronic apparatus includes a sensor, a power storage element, and a communication module.

The sensor generates charge in accordance with a surrounding environment.

The power storage element accumulates the generated charge.

The communication module includes an electric power supply unit and a communication processing unit.

The electric power supply unit supplies electric power by generating electric power with energy in a surrounding environment.

The communication processing unit is configured to be capable of being switched between a stand-by state and an operating state on the basis of the electric power supplied from the electric power supply unit and is configured to be capable of acquiring accumulation information of the charge from the power storage element and outputting the accumulation information in the operating state.

The processing apparatus generates information on a surrounding environment of the electronic apparatus on the basis of the output accumulation information.

Advantageous Effects of Invention

As described above, according to the present technology, it is possible to provide an electronic apparatus, an information processing method therefor, and an information processing system including an electronic apparatus, which are capable of achieving electric power saving and acquiring environment information in a stand-by state.

Note that the effects described herein are not necessarily limitative and any effect described in the present disclosure may be provided.

BRIEF DESCRIPTION OF DRAWINGS

FIG. 4 is a flowchart describing an example of a flow of processing when the electronic apparatus outputs accumulation information and the like.

FIG. 19 is a flowchart describing an example of a flow of processing when the electronic apparatus outputs accumulation information and the like.

MODE(S) FOR CARRYING OUT THE INVENTION

Hereinafter, embodiments according to the present technology will be described with reference to the drawings.

First Embodiment

[Configuration of Electronic Apparatus]

Figure 1:
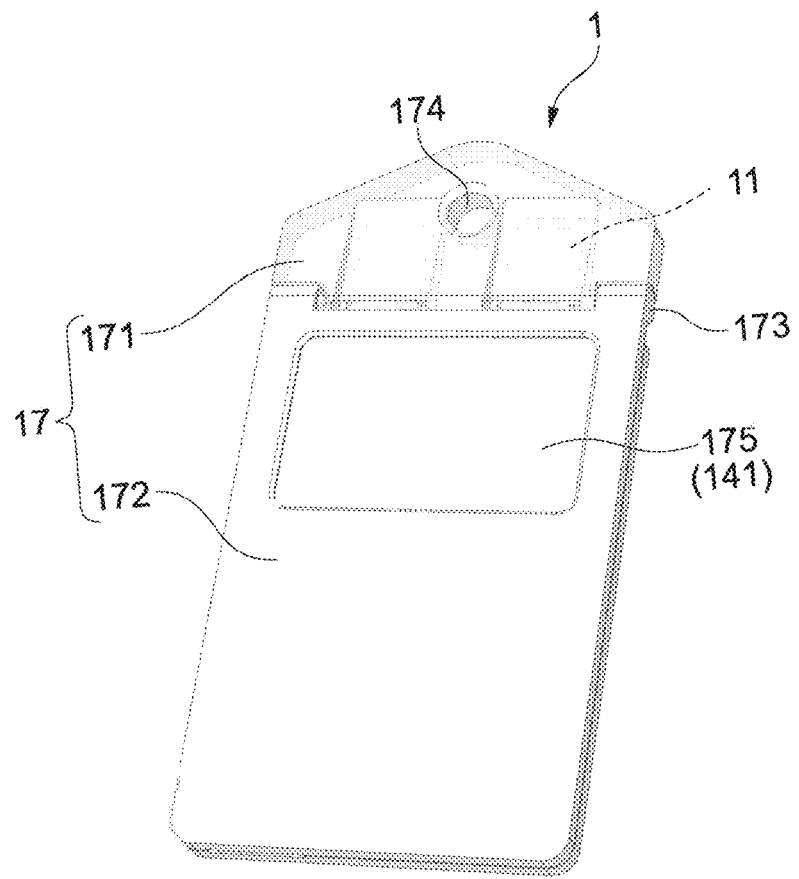
FIG. 1 is a perspective view showing an example of an outer appearance of an electronic apparatus according to a first embodiment of the present technology.

FIG. 1 is a perspective view showing one example of an outer appearance of an electronic apparatus according to this embodiment.

In this embodiment, an electronic apparatus 1 is configured to be attachable to a living body of a human or an animal. For example, the electronic apparatus 1 may be directly attached to a living body with use of an attachment tool and the like. Alternatively, the electronic apparatus 1 may be indirectly attached by being attached to belongings (bag and the like) carried by or attached to the living body. Alternatively, the electronic apparatus 1 may be configured to be attachable to a non-living body such as transported goods of logistics.

The electronic apparatus 1 is configured to have a substantially rectangular parallelepiped shape that is thin as a whole and configured to have a portable size. For example, the size of the electronic apparatus 1 is configured to be approximately 20 to 100 mm in longitudinal length by 10 to 50 mm in lateral length by 1 to 10 mm in thickness.

The electronic apparatus 1 functions as a sensor apparatus that acquires, for example, information on a surrounding environment, and is configured to be communicable with an external apparatus. The electronic apparatus 1 is configured to be attachable, and can thus output information on behavior, a state, and the like of a human or animal to which the electronic apparatus 1 is attached, in addition to the weather around the electronic apparatus 1 and the like.

(Casing)

As shown in FIG. 1, the electronic apparatus 1 includes a casing 17.

The casing 17 is formed of, for example, a resin material such as an ABS resin, a polycarbonate resin, a polylactic acid, and a polyamide resin. As will be described later, the casing 17 may be formed of a material, at least a part of which is capable of causing light of a predetermined wavelength (solar light or the like) or electromagnetic waves to pass therethrough. Alternatively, the casing 17 may be a combination of wood or a resin material having no transmittivity and glass or a resin having transmittivity.

Further, considering the safety for the environment and living bodies, a material including a plant-derived material, an antiallergic material, an antibacterial material, or the like can be appropriately selected as the material of the casing 17. Furthermore, a food additive disliked by animals may be mixed therein for preventing accidental ingestion.

Further, the casing 17 may be configured to be capable of being accommodated in a case. Such a case may be provided with a decoration or a function. With this, variations in structure, color, pattern, and the like of the casing 17 are limited while corresponding to a request or taste of a target for use, so that manufacturing costs can be suppressed.

Referring to FIG. 1, the casing 17 includes a tab 171, a main body 172, and a hinge 173 that connects the tab 171 and the main body 172.

The tab 171 is configured to be capable of changing its posture to the main body 172 by an action of the hinge 173. For example, the tab 171 is configured to be capable of rotating about the hinge 173 (e.g., see FIGS. 29 to 35).

The tab 171 includes, for example, a hole for attachment 174. If a target to which the electronic apparatus 1 is attached is a human, an attachment tool such as a string or a chain can be fixed to the hole 174, to attach the electronic apparatus 1 to the neck, an arm, the waist, or belongings such as a bag. Further, if a target to which the electronic apparatus 1 is attached is an animal such as a dog or a cat, an attachment tool such as a string or a chain can be fixed to the hole 174, to attach the electronic apparatus 1 to a collar or the like. If a target to which the electronic apparatus 1 is attached is a livestock animal such as beef cattle, the electronic apparatus 1 may be attached to the vicinity of an earmark for individual identification via the hole 174.

The main body 172 is configured to have a rectangular parallelepiped shape that is thin as a whole.

The main body 172 includes, for example, a window portion 175. The window portion 175 may be formed of a translucent material capable of causing light such as solar light to pass therethrough, or may be configured as an opening. On the inner side of the window portion 175, a solar battery (solar cell) included in a power generation element 141, which will be described later, can be disposed.

A configuration of the hinge 173 is not particularly limited, but the hinge 173 is configured such that the tab 171 can easily change its posture to the main body 172 in accordance with, for example, a motion of a target to which the electronic apparatus 1 is attached.

Figure 2:
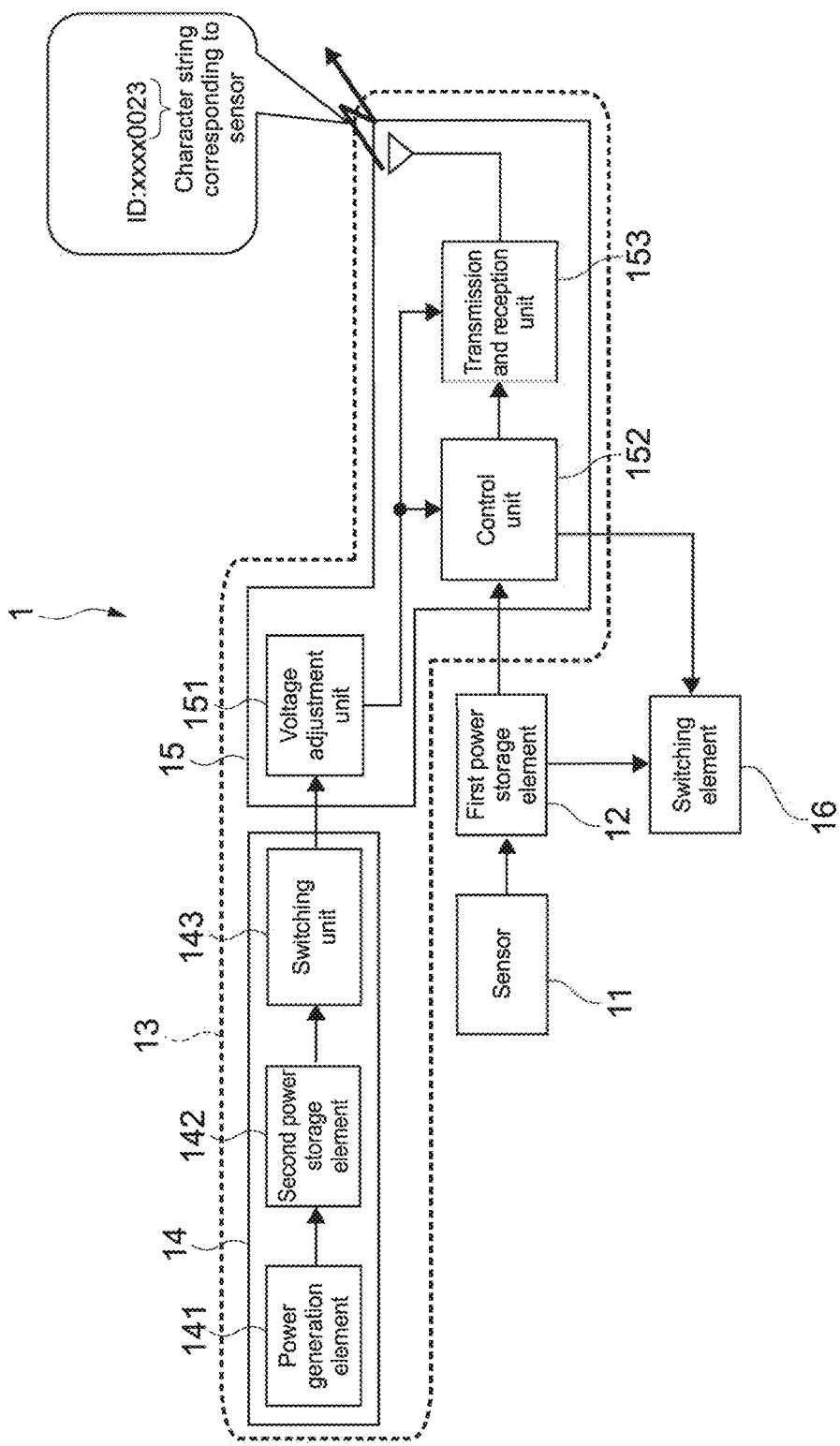
FIG. 2 is a block diagram showing a configuration of the electronic apparatus.
Figure 3:
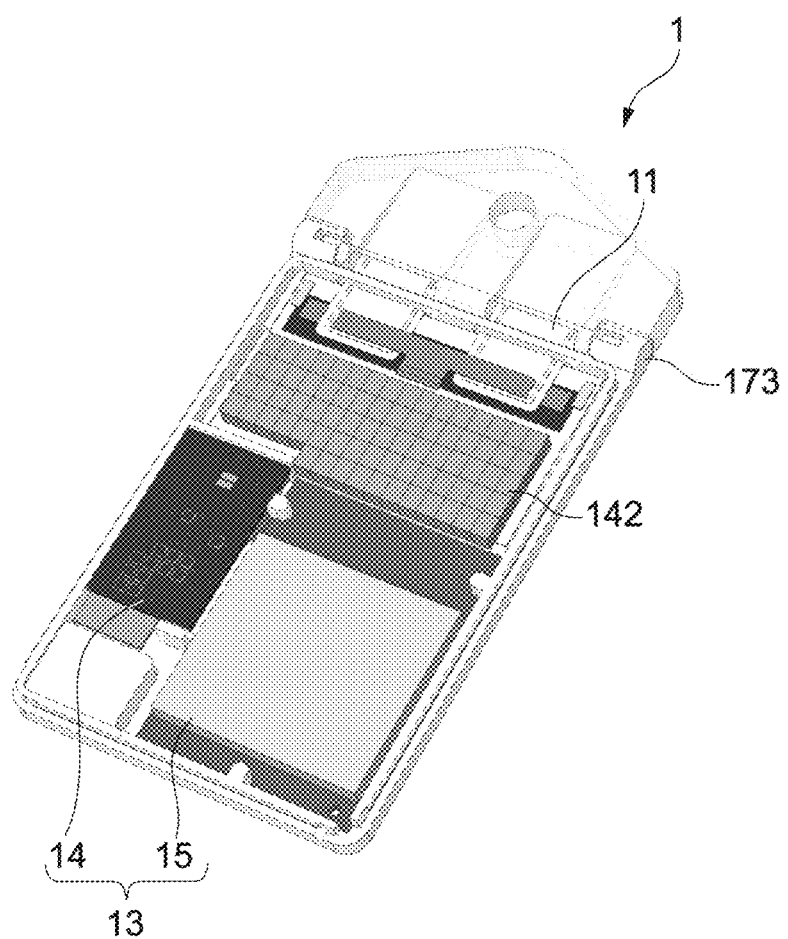
FIG. 3 is a perspective view showing an example of the internal structure of the electronic apparatus.

FIG. 2 is a block diagram showing a configuration of the electronic apparatus 1. Further, FIG. 3 is a diagram showing an example of the internal structure of the electronic apparatus 1 and is also a perspective view showing a mode in which a part of the casing of the electronic apparatus 1 is removed.

As shown in the figures, the electronic apparatus 1 includes a sensor 11, a first power storage element (power storage element) 12, a communication module 13, and a switching element 16. Hereinafter, those elements will be described.

(Sensor)

The sensor 11 generates charge in accordance with a surrounding environment. A charge generation method can be of a piezoelectric type, an electrostatic type, an inverse magnetostrictive type, an electromagnetic type, or the like.

The sensor 11 may generate charge in accordance with, for example, vibrations. Vibrations include vibration involved in a motion of a user. Further, the sensor 11 may generate charge by deformation corresponding to vibrations. Specifically, the sensor 11 may be a vibration power generation element, an acceleration sensor, an angular velocity sensor, a geomagnetic sensor, or the like. The vibration power generation element may have a well-known configuration and may use a piezoelectric element including, for example, an inorganic material or an organic material.

The sensor 11 may generate charge in accordance with a temperature difference. Specifically, the sensor 11 may be a thermoelectric conversion element that generates charge by utilizing a temperature difference (heat) (e.g., one that generates electric power by using the Seebeck effect and the Thomson effect, thermionic power generation element, or one that performs thermomagnetic generation). Such a sensor 11 can generate charge by utilizing, for example, a temperature difference between a body temperature of a human body or an animal and an ambient temperature.

The sensor 11 may generate charge in accordance with light irradiation. The light includes solar light and an indoor light bulb. Specifically, the sensor 11 can use a solar power generation element having a well-known configuration.

The sensor 11 may generate charge by a near or far electromagnetic field of the sensor 11. For example, the sensor 11 can have a configuration to acquire energy from electromagnetic waves emitted from an adjacent predetermined device and generate charge. Alternatively, the sensor 11 may have a configuration to acquire energy from electromagnetic waves emitted from a predetermined device disposed in the distance and generate charge.

The sensor 11 may generate charge in accordance with energy generated by an ion concentration difference. For example, the sensor 11 can have a configuration to generate charge in accordance with energy by an ion concentration gradient of sodium ions or the like generated when seawater and fresh water are mixed.

The sensor 11 may generate charge in accordance with energy generated by a chemical reaction. Specifically, the sensor 11 may be an enzyme battery (also called bio-battery or the like) that generates charge by utilizing glucose or the like.

The sensor 11 may generate charge in accordance with sound. Specifically, the sensor 11 may be a microphone such as a dynamic microphone, an electret capacitor microphone, or a piezoelectric microphone.

In addition to the above, the sensor 11 is not particularly limited as long as the sensor 11 generates an electric signal corresponding to the environment.

Note that the sensor 11 may be grounded.

If the sensor 11 generates charge in accordance with vibrations, the sensor 11 may be disposed so as to be capable of vibrating on the basis of the change in posture of the tab 171 to the main body 172. For example, if the sensor 11 generates charge by deformation corresponding to vibrations, the sensor 11 may be disposed so as to be capable of deforming on the basis of the change in posture of the tab 171 to the main body 172.

Specifically, as shown in FIG. 3, the sensor 11 may be disposed over both of the main body 172 and the tab 171.

With this, the sensor 11 can efficiently generate charge in accordance with vibrations.

(Power Storage Element)

The first power storage element 12 accumulates the charge generated by the sensor 11. The first power storage element 12 is, for example, connected to the sensor 11 via one of terminals and is grounded via the other terminal.

The first power storage element 12 may be, for example, a capacitor. With this, a voltage value becomes proportional to a charge accumulation amount, and the charge accumulation amount can thus be easily estimated from the voltage value. The capacitor can be a ceramic capacitor, a film capacitor, an aluminum electrolytic capacitor, a tantalum capacitor, and the like.

Alternatively, the first power storage element 12 may be various secondary batteries such as a lithium-ion secondary battery, an electric double layer capacitor, a lithium ion capacitor, a polyacenic semiconductor (PAS) capacitor, a Nanogate capacitor ("Nanogate" is a registered trademark of Nanogate Aktiengesellschaft), and the like. Further, the first power storage element 12 may be a combination of those power storage elements.

(Communication Module)

The communication module 13 includes an electric power supply unit 14 and a communication processing unit 15 and is configured to be capable of outputting accumulation information of the charge of the first power storage element 12, and the like.

The electric power supply unit 14 supplies electric power by generating electric power with energy in a surrounding environment. Specifically, the electric power supply unit 14 includes a power generation element 141, a second power storage element 142, and a switching unit 143. The electric power supply unit 14 causes the second power storage element 142 to accumulate the electric power generated by the power generation element 141 and supplies the electric power to the communication processing unit 15 via the switching unit 143.

The power generation element 141 generates electric power in accordance with a surrounding environment. The power generation element 141 may generate electric power with energy based on at least any one of, for example, light, heat, vibrations, radio waves including a far electromagnetic field and a near electromagnetic field, and particular organic and inorganic matters. A power generation method can be of an electrostatic type, an electromagnetic type, an inverse magnetostrictive type, a piezoelectric type, and the like.

The power generation element 141 may generate electric power with light (e.g., indoor light bulb and solar light).

The power generation element 141 may be a thermoelectric conversion element that generates electric power by utilizing a temperature difference (heat) (e.g., one that generates electric power by using the Seebeck effect and the Thomson effect, thermionic power generation element, or one that performs thermomagnetic generation). Such a power generation element 141 generates electric power by utilizing, for example, a temperature difference between a body temperature of a human body or an animal and an ambient temperature.

The power generation element 141 may be an enzyme battery (also called bio-battery or the like) that generates electric power by utilizing glucose.

The power generation element 141 utilizes any of LCR (inductance, capacitance, and reactance) components or a combination thereof and capacitive coupling or electromagnetic coupling with a capacitor, an antenna, a rectenna, and the like. The power generation element 141 may generate electric power with radio waves, for example.

The power generation element 141 may perform near electromagnetic field power generation, that is, generate electric power with energy obtained by bringing an electronic apparatus close to a predetermined device. A well-known method such as a magnetic field resonance method, an electromagnetic induction method, electric field coupling, and an electric field resonance method can be applied to a method for near electromagnetic field power generation.

A well-known power generation element other than those exemplified above can be applied to the power generation element 141.

The second power storage element 142 is used in a manner that depends on purposes of, for example, storing electric power generated by the power generation element 141. The second power storage element 142 is, for example, connected to the power generation element 141 via one of terminals and is grounded via the other terminal.

Besides various secondary batteries such as a lithium-ion secondary battery, the second power storage element 142 includes an electric double layer capacitor, a lithium ion capacitor, a polyacenic semiconductor (PAS) capacitor, a Nanogate capacitor ("Nanogate" is a registered trademark of Nanogate Aktiengesellschaft), a ceramic capacitor, a film capacitor, an aluminum electrolytic capacitor, a tantalum capacitor, and the like. Further, the second power storage element 142 may be a combination of those power storage elements.

The switching unit 143 is connected between the second power storage element 142 and the communication processing unit 15 and is switched between a conduction state and a blocking state. More specifically, when the amount of electric power generated with energy in a surrounding environment is a predetermined electric power amount or more, the switching unit 143 is switched from a blocking state in which supply of electric power to the communication processing unit 15 is blocked to a conduction state in which electric power is supplied to the communication processing unit 15. After being switched to the conduction state, the switching unit 143 is switched to the blocking state again and blocks supply of electric power to the communication processing unit 15. The "predetermined electric power amount" can be, for example, an electric power amount that is equal to or larger than an electric power amount with which the communication processing unit 15 can be operated for a predetermined time.

The switching unit 143 can use, for example, a voltage value or electric field value in the second power storage element 142, a charge amount accumulated in the second power storage element 142, or the like, as a determination reference of the electric power amount supplied from the electric power supply unit 14.

Specifically, the switching unit 143 includes, for example, an integrated circuit (IC) formed of one or more elements. Examples of the integrated circuit can include a switching element such as a transistor, a diode, a reset IC, a regulator IC, a logic IC, and various arithmetic circuits. A circuit configuration inside the IC can be appropriately changed as long as it can realize the function of the switching unit 143. Alternatively, the switching unit 143 may have a configuration including an electric field reaction type switch that switches between conduction and blocking in accordance with an electric field magnitude, and the like.

The switching unit 143 can reduce the burden of executing determination processing by a control unit 152, which will be described later, or the like and can suppress electric power consumption.

The communication processing unit 15 is configured to be capable of being switched between a stand-by state and an operating state on the basis of the electric power supplied from the electric power supply unit 14. The communication processing unit 15 is configured to be capable of acquiring charge accumulation information from the first power storage element 12 and outputting the accumulation information in the operating state. For example, when being provided with the electric power supplied from the electric power supply unit 14, the communication processing unit 15 is switched from the stand-by state to the operating state, and when consuming the supplied electric power in the operating state, the communication processing unit 15 is switched from the operating state to the stand-by state.

In this embodiment, when the switching unit 143 is switched from the blocking state to the conduction state, the communication processing unit 15 is provided with electric power from the electric power supply unit 14 and can be switched from the stand-by state to the operating state.

For example, the communication processing unit 15 includes a voltage adjustment unit 151, a control unit 152, and a transmission and reception unit 153.

The voltage adjustment unit 151 increases or decreases an input voltage from the electric power supply unit 14 on the basis of an operating voltage of the control unit 152 so as to keep an output voltage constant. Specifically, the voltage adjustment unit 151 includes a DC-DC converter of a switching method, a linear method, or the like, a resistance element, and the like. Of those, the DC-DC converter of a switching method is favorable for the purpose of efficiently using energy.

The control unit 152 acquires charge accumulation information from the first power storage element 12 in the operating state. The control unit 152 also executes transmission control of the transmission and reception unit 153.

The charge accumulation information may include, for example, information of the voltage value of the first power storage element 12, which is based on the accumulated charge.

Specifically, the control unit 152 includes a processor and memories such as a ROM (Read Only Memory) and a RAM (Random Access Memory). Examples of the processor can include an MPU (Micro Processing Unit) and a CPU (Central Processing Unit). The MPU is more favorable as the processor because of the throughput of the communication processing unit 15 and a requirement for downsizing of the electronic apparatus 1. Further, the control unit 152 may be configured as a microcontroller obtained by mounting the processor, the ROM, and the RAM on one chip. With this, the number of components can be reduced, and downsizing can be realized.

The transmission and reception unit 153 is controlled by the control unit 152 and outputs charge accumulation information.

The communication performed by the transmission and reception unit 153 may be wireless or may be wired. Further, a wireless module used as the transmission and reception unit 153 may be single, may be of various types, or may be a composite module including the various types. The wireless communication may be communication utilizing electromagnetic waves (including infrared rays) or may be communication utilizing an electric field. Examples of a specific method therefor can include communication methods utilizing a band of several hundreds MHz (megahertz) to several GHz (gigahertz), such as "Wi-Fi (registered trademark)", "Zigbee (registered trademark)", "Bluetooth (registered trademark)", "Bluetooth Low Energy", "ANT (registered trademark)", "ANT+ (registered trademark)", and "EnOcean (registered trademark)". Note that a frequency band used for communication is not limited to the above. Alternatively, proximity wireless communication such as NFC (Near Field Communication) may be employed.

Furthermore, the transmission and reception unit 153 (communication processing unit 15) may output identification information of the sensor 11, which is associated with the charge accumulation information, in the operating state. With this, an external apparatus that has received the accumulation information can easily determine to which sensor 11 the received accumulation information corresponds.

If the electronic apparatus 1 includes only one sensor 11, the identification information of the sensor 11 may be information with which the electronic apparatus 1 can be identified. Alternatively, the identification information of the sensor 11 may include, in at least a part thereof, information with which the sensor 11 can be identified.

The identification information may be set in advance. Alternatively, the identification information may be generated each time the electronic apparatus 1 establishes communication connection with an external apparatus.

Further, the identification information may be an identifier (ID: identification) formed of a predetermined character string. FIG. 2 shows an example of the identifier. As shown in the figure, the identifier may include a character string with which the sensor 11 can be identified (see the figure).

(Switching Element)

The switching element 16 is connected to the first power storage element 12. After the communication processing unit 15 acquires the charge accumulation information, the switching element 16 is controlled by the communication processing unit 15 so as to discharge the charge accumulated in the first power storage element 12.

The switching element 16 can have a configuration including, for example, a semiconductor switch or transistor switch using a CMOS or the like. Further, the switching element 16 is typically connected to the first power storage element 12 via one of terminals and is grounded via the other terminal.

The switching element 16 may be controlled to be switched by the control unit 152. That is, the switching element 16 is generally maintained in a state where charge can be accumulated by the first power storage element 12 (e.g., blocking state), but after read of the accumulation information is executed by the control unit 152, the switching element 16 is switched to a state where the charge is discharged (e.g., conduction state). Further, after switched to the conduction state, the switching element 16 may be switched to the blocking state again when the communication module 13 returns to the stand-by state.

[Operation Example of Electronic Apparatus]

A typical operation example of the electronic apparatus 1 having the configuration described above will be described.

Figure 4:
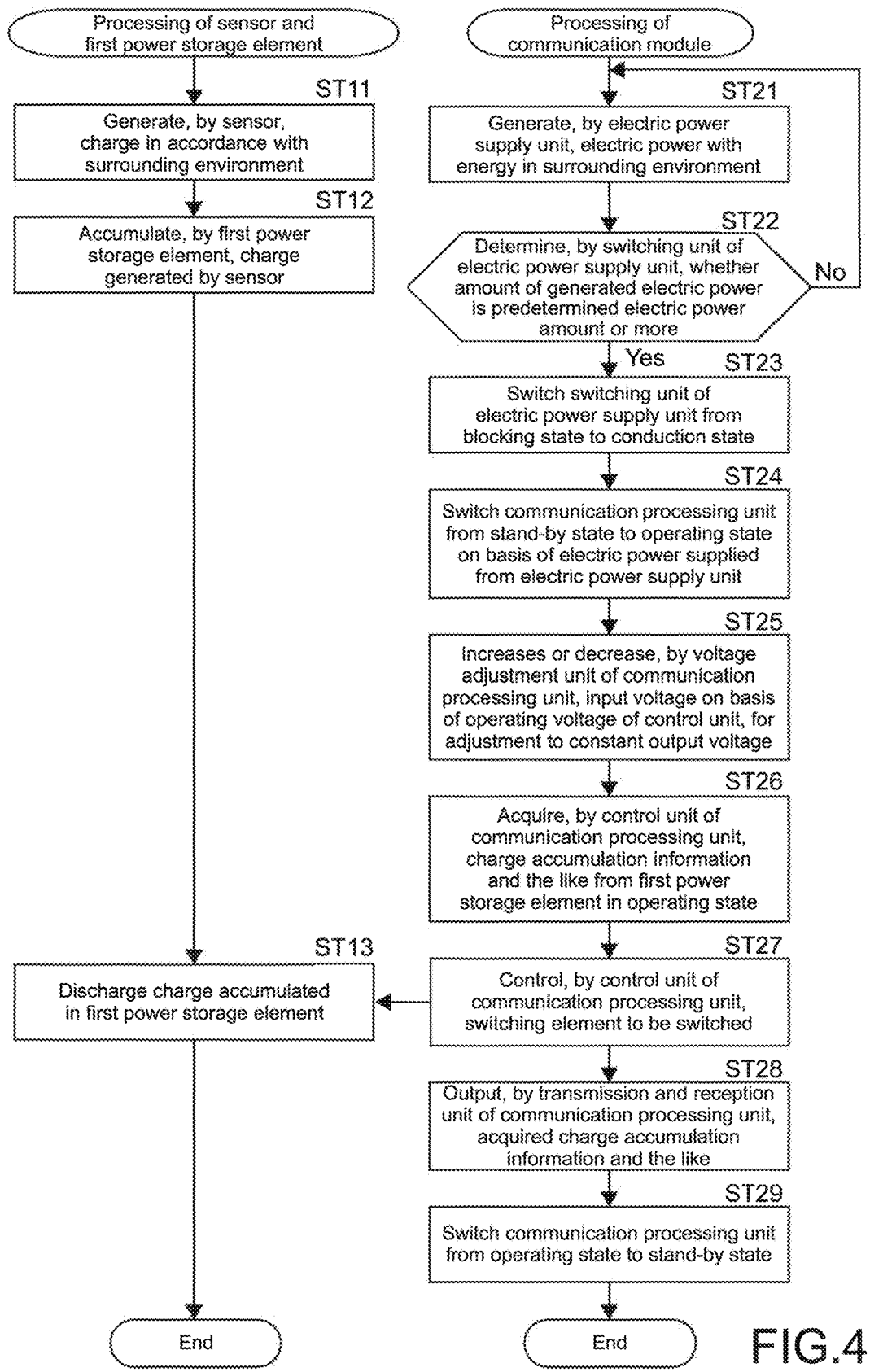

FIG. 4 is a flowchart describing an example of a flow of processing when the electronic apparatus 1 outputs accumulation information and the like. In the figure, ST11 to ST13 are executed by the sensor 11 and the first power storage element 12, and ST21 to ST13 are executed by the communication module 13. Note that here description will be given assuming that the sensor 11 is a vibration power generation element that generates charge in accordance with vibrations, and the power generation element 141 is an element capable of generating solar power.

Firstly, the sensor 11 generates charge in accordance with a surrounding environment (ST11).

For example, the sensor 11 vibrates in accordance with a motion of a user (including a human and an animal) to which the electronic apparatus 1 is attached. The sensor 11 generates charge.

Subsequently, the first power storage element 12 accumulates the charge generated by the sensor 11 (ST12).

As the charge is generated from the sensor 11, the charge is accumulated in the first power storage element 12 such as a capacitor. With this, a voltage corresponding to the accumulation of the charge is generated in the first power storage element 12.

Meanwhile, the electric power supply unit 14 of the communication module 13 generates electric power with energy in a surrounding environment (ST21).

Specifically, the power generation element 141 first generates electric power. For example, when a user wearing the electronic apparatus 1 goes outside in fine weather, the power generation element 141 is irradiated with solar light, and thus the power generation element 141 generates electric power.

Subsequently, the electric power generated by the power generation element 141 is accumulated as charge in the second power storage element 142 such as a capacitor. Also in this case, a voltage corresponding to the accumulation of the charge is generated in the second power storage element 142.

Subsequently, the switching unit 143 determines whether the amount of the electric power generated with energy in a surrounding environment is a predetermined electric power amount or more (ST22). That is, the switching unit 143 determines whether the voltage of the second power storage element 142 is higher than a reference voltage.

If it is determined that the amount of the electric power is less than the predetermined electric power amount (No in ST22), the processing returns to ST21.

If it is determined that the amount of the electric power is the predetermined electric power amount or more, the switching unit 143 is switched from the blocking state to the conduction state (ST23).

Note that the processing of ST22 and ST23 in this operation example depends on that the state of the switching unit 143 is switched when the voltage of the second power storage element 142 is a reference voltage or more. The determination processing of ST22 is not performed by a certain functional block.

Subsequently, the communication processing unit 15 of the communication module 13 is switched from the stand-by state to the operating state on the basis of the electric power supplied from the electric power supply unit 14 (ST24).

Specifically, the switching unit 143 is switched to the conduction state, the electric power generated by the electric power supply unit 14 is supplied to the communication processing unit 15, and thus the communication processing unit 15 is switched to the operating state.

After being switched to the operating state, the voltage adjustment unit 151 of the communication processing unit 15 increases or decreases an input voltage on the basis of an operating voltage of the control unit 152 so as to keep an output voltage constant (ST25).

Subsequently, the control unit 152 of the communication processing unit 15 acquires the charge accumulation information from the first power storage element 12 in the operating state and also acquires the identification information of the sensor 11, which is stored in the ROM or the like (ST26).

For example, the control unit 152 acquires, as charge accumulation information, information of a voltage value of the first power storage element 12 that is based on the accumulated charge.

Specifically, the control unit 152 reads a program stored in, for example, the ROM and executes processing corresponding to a code described in the program.

Subsequently, the control unit 152 controls the switching element 16 to be switched from the blocking state to the conduction state (ST27). With this, the first power storage element 12 discharges the accumulated charge (ST13).

Subsequently, the transmission and reception unit 153 of the communication processing unit 15 outputs the acquired charge accumulation information and the identification information of the sensor (ST28).

At that time, the transmission and reception unit 153 is provided with electric power from the voltage adjustment unit 151 and the control unit 152 and is controlled by the control unit 152. Specifically, the transmission and reception unit 153 is instructed to start transmission by the control unit 152 and is controlled to output the accumulation information and the identifier.

Lastly, because of consumption of the supplied electric power, the communication processing unit 15 is switched from the operating state to the stand-by state again (ST29). At that time, the control unit 152 may control the switching element 16 to be switched from the conduction state to the blocking state.

The electronic apparatus 1 repeats the processing, which includes the steps described above, as one cycle.

[Action of Operation Example in this Embodiment]

Figure 5:
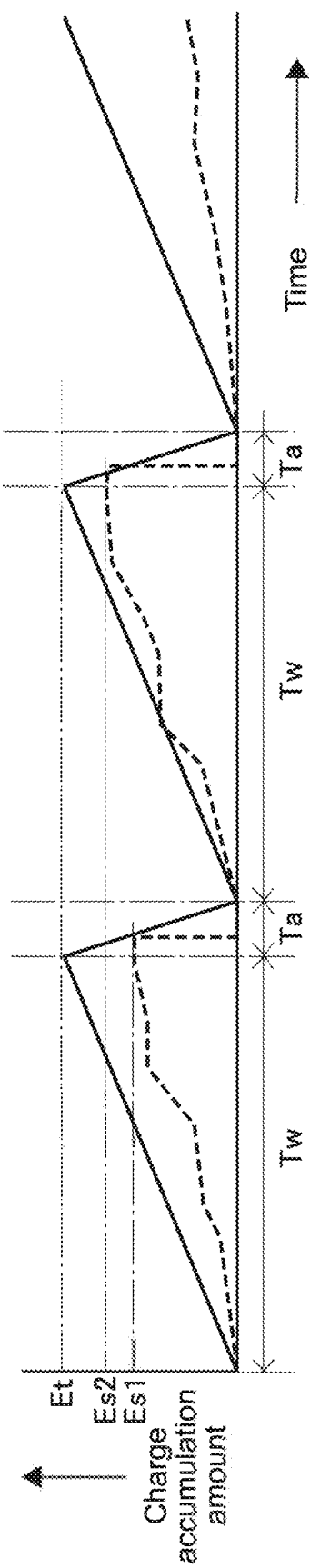
FIG. 5 is a graph showing charge accumulation amounts of a first power storage element and a second power storage element of the electronic apparatus in an operation example described with reference to FIG. 4.

FIG. 5 is a graph showing the charge accumulation amounts of the first power storage element 12 and the second power storage element 142 in the operation example described with reference to FIG. 4, in which the horizontal axis represents a time, and the vertical axis represents a charge accumulation amount. Further, in the graph, a solid line represents the charge accumulation amount of the second power storage element 142, and a broken line represents the charge accumulation amount of the first power storage element 12. A time Tw represents a stand-by state, and a time Ta represents an operating state.

Firstly, referring to the charge accumulation amount of the second power storage element 142 represented by the solid line, the charge accumulation amount is gradually increased by the power generation of the power generation element 141 (ST21 of FIG. 4).

When the charge accumulation amount of the second power storage element 142 reaches a predetermined charge accumulation amount Et, the switching unit 143 is switched from the blocking state to the conduction state (ST22 and ST23 of FIG. 4), and the communication processing unit 15 is switched to the operating state to executes the processing (ST24 to ST28 of FIG. 4). In this period, the charge accumulation amount of the second power storage element 142 is gradually lowered. This is because the charge accumulated in the second power storage element 142 is being consumed by the processing of the communication processing unit 15.

The communication processing unit 15 then returns to the stand-by state again (ST29 of FIG. 4), and the charge accumulation amount of the second power storage element 142 starts to increase.

Note that the transition of the charge accumulation amount of the second power storage element 142 shown in FIG. 5 is an example, and the charge accumulation amount may not be zero at a point at which the charge accumulation amount starts to increase. Hereinafter, the same holds true for the transition of the charge accumulation amount of the first power storage element 12 shown in FIG. 5, and the transition of a charge accumulation amount shown in FIG. 8, which will be described later.

Meanwhile, referring to the charge accumulation amount of the first power storage element 12 represented by the broken line, the sensor 11 generates charge in the stand-by state corresponding to ST11 and ST12 of FIG. 4, and thus the charge accumulation amount is gradually increased. The control unit 152 switched to the operating state then acquires a charge accumulation amount Esk of the first power storage element 12 (k represents a cycle number from the operation start of the electronic apparatus 1) (ST26 of FIG. 4). The Esk is not a constant value but an accumulation amount that is accumulated when the charge accumulation amount Esk of the first power storage element 12 is acquired.

After reaching the charge accumulation amount Esk, the charge accumulation amount of the first power storage element 12 sharply decreases. This is because, as described above, the switching element 16 is temporarily switched to the conduction state in ST27, and thus the charge stored in the first power storage element 12 is discharged in ST13.

The switching element 16 then returns to the stand-by state again, and the charge accumulation amount of the first power storage element 12 starts to increase.

In such a manner, according to the electronic apparatus 1 of this embodiment, the charge accumulation amount of the first power storage element 12, which is accumulated from the start of the stand-by state to the step of acquiring the charge accumulation amount of the first power storage element 12 (ST26 of FIG. 4), can be output. That is, the electronic apparatus 1 can output the charge accumulation information generated by the sensor 11 in the stand-by state.

Action and Effect of this Embodiment

Hereinafter, the action and effect of this embodiment will be specifically described using a comparison example.

Figure 6:
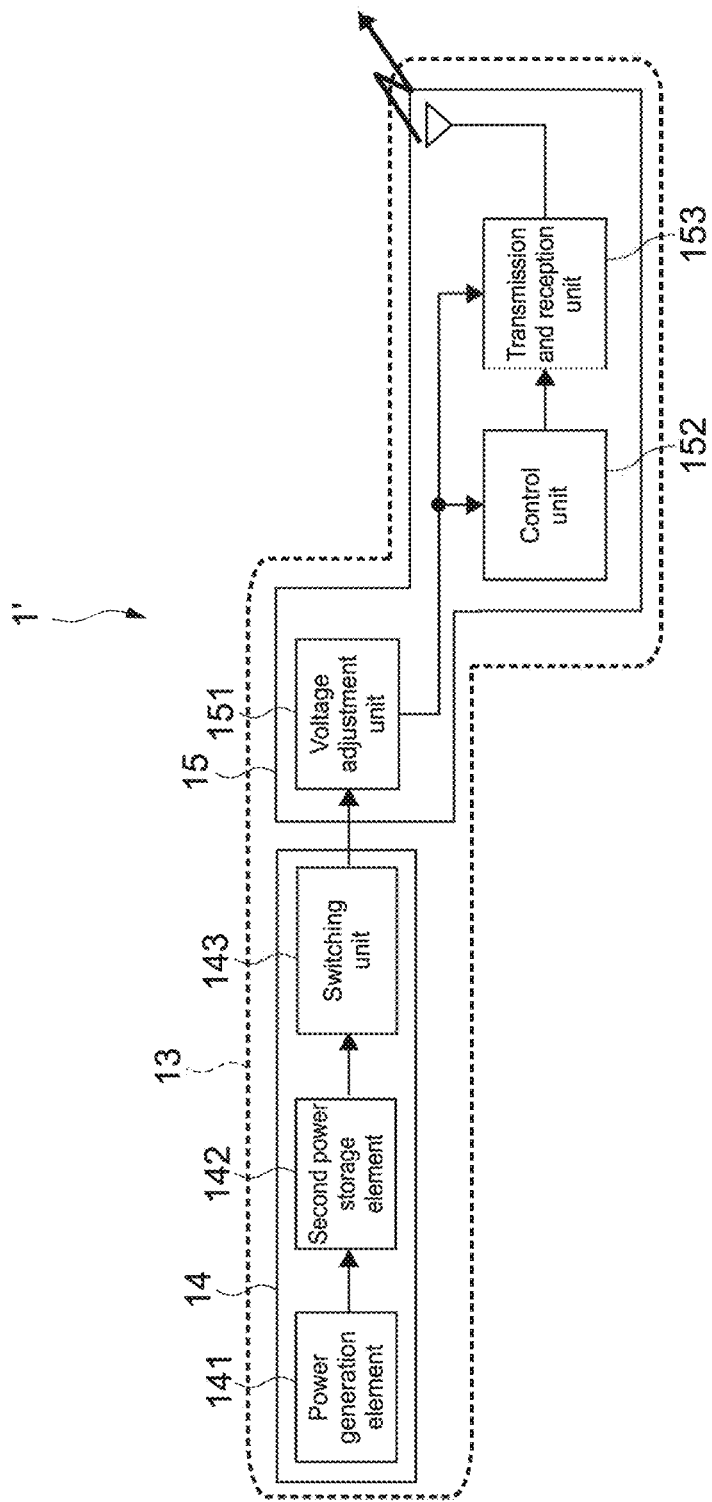
FIG. 6 is a block diagram showing a configuration of an electronic apparatus according to a comparison example of the first embodiment.

FIG. 6 is a block diagram showing a configuration of an electronic apparatus 1' according to a comparison example of this embodiment. The electronic apparatus 1' includes a communication module 13 having a configuration similar to that of this embodiment, but does not include configurations corresponding to the sensor 11 and the first power storage element 12. The communication module 13 can output identification information of a power generation element 141 in an operating state.

In this case, an external apparatus, which has received the identification information, refers to the graph on the second power storage element 142 represented by the solid line of FIG. 5, and analyzes an interval at which the charge accumulation amount of the second power storage element 142 is a predetermined charge accumulation amount Et, that is, an operation interval. Thus, the external apparatus can indirectly estimate a power generation amount of the power generation element 141. However, the external apparatus cannot acquire information such as an actual power generation amount or a charge accumulation amount in the stand-by state.

Further, assuming that the electronic apparatus 1' includes a sensor connected to the communication module 13 (not shown), when information of the sensor in the stand-by state is intended to be acquired, it is necessary to constantly operate and monitor the control unit 142 of the communication module 13. This increases power consumption. In order to cope with the increase in power consumption, it is necessary to mount a secondary battery and the like in addition to the power generation element 141, and there arises a risk that the configuration of the apparatus is increased in size.

Meanwhile, according to this embodiment, since the charge generated in accordance with the environment can be accumulated, it is not necessary to constantly operate the control unit 152, and the charge accumulation information accumulated in the operating state only needs to be acquired. With this, the environment information in the stand-by state can be acquired while suppressing power consumption.

Further, according to this embodiment, even when the amount of charge generated in accordance with an environment is small and electric power enough to operate the control unit 152 cannot be supplied, the communication processing unit 15 can acquire accumulation information related to this charge amount. That is, the sensor 11 is not limited to a so-called energy harvesting element. With this, the degree of freedom of the configuration of the sensor 11 can be enhanced, and the electronic apparatus 1 can realize reduction in size and electric power saving and provide a variety of information corresponding to needs.

Reference Example

Meanwhile, if the sensor has a large charge generation amount, and electric power capable of operating a communication processing unit can be supplied, the following configuration can be applied.

Figure 7:
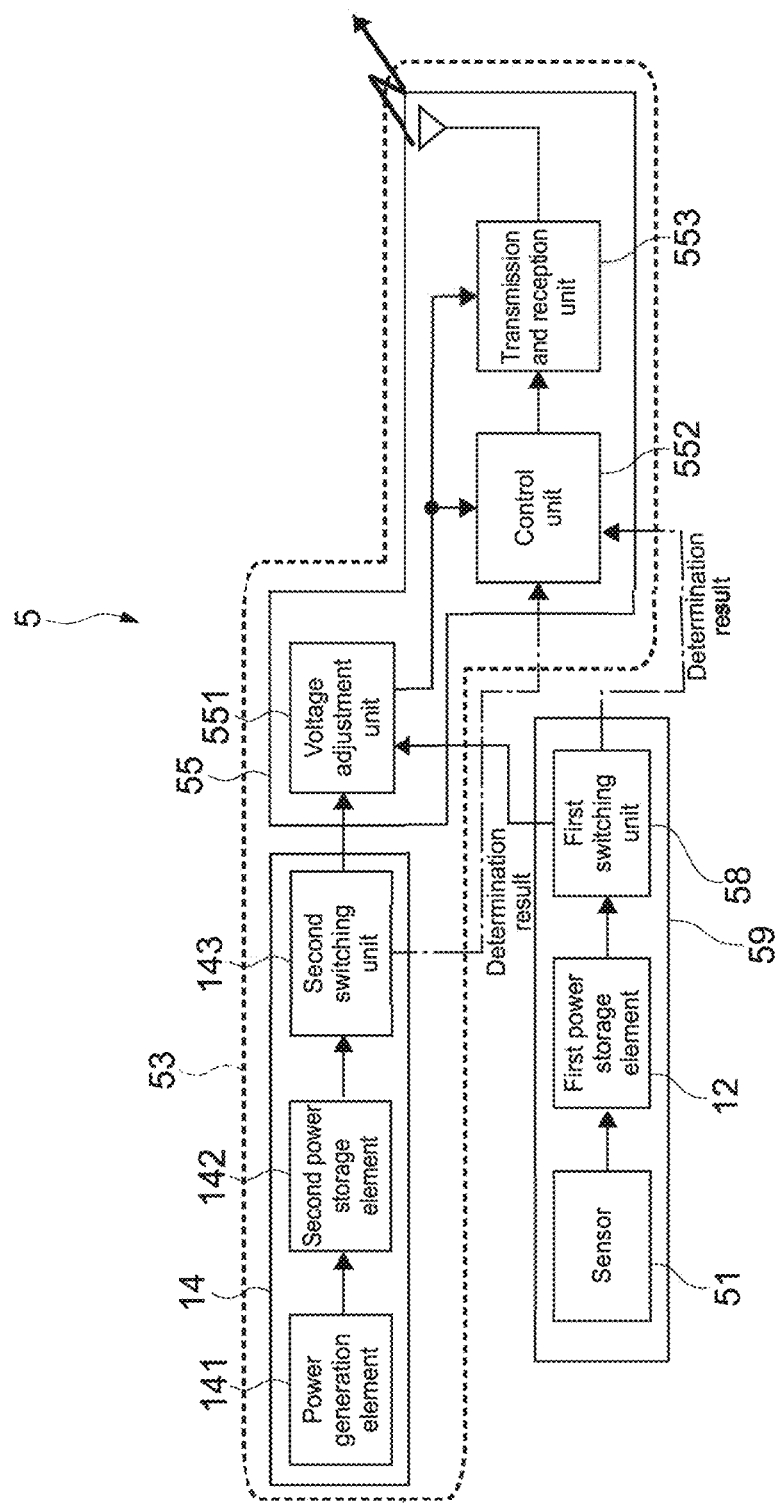
FIG. 7 is a block diagram showing a configuration of an electronic apparatus according to a reference example.

FIG. 7 is a block diagram showing a configuration of an electronic apparatus according to a reference example.

An electronic apparatus 5 is configured such that a sensor and a first power storage element have similar functions as that of an electric power supply unit of a communication module, and the state of the communication processing unit is switchable by the supply of electric power from the sensor and the first power storage element.

Note that in the following description configurations similar to those of the electronic apparatus 1 will be denoted by identical reference signs and detailed descriptions thereof will be omitted.

As shown in FIG. 7, the electronic apparatus 5 includes a sensor 51, a first switching unit 58, a first power storage element 12, and a communication module 53.

The sensor 51 generates charge in accordance with a surrounding environment. In this reference example, the sensor 51 employs a power generation element capable of generating power. Charge generated by the sensor 51 is accumulated in the first power storage element 12.

The first switching unit 58 is connected between the first power storage element 12 and a communication processing unit 55 that will be described later. When the amount of the electric power generated by the sensor 51 is a predetermined electric power amount or more, the first switching unit 58 is switched from a blocking state in which supply of electric power to the communication processing unit 55 is blocked to a conduction state in which electric power is supplied to the communication processing unit 55. The first switching unit 58 can be configured similarly to a second switching unit 143.

The sensor 51, the first power storage element 12, and the first switching unit 58 function as a first electric power supply unit 59.

The communication module 53 includes a second electric power supply unit (electric power supply unit) 14 and the communication processing unit 55.

The second electric power supply unit 14 includes a power generation element 141, a second power storage element 142, and a second switching unit 143.

The communication processing unit 55 is configured to be switchable between a stand-by state and an operating state on the basis of the electric power supplied from at least one of the first and second electric power supply units 39 and 14, and is configured to be capable of outputting identification information of each of the electric power supply units 39 and 14. With this, an external apparatus, which has received the identification information, can determine from which of the electric power supply units 39 and 14 electric power is supplied to perform communication processing.

The communication processing unit 55 includes a voltage adjustment unit 451, a control unit 452, and a transmission and reception unit 453, which are configured similarly to the voltage adjustment unit 151, the control unit 152, and the transmission and reception unit 153 described above, respectively.

The voltage adjustment unit 451 is connected to both the first and second switching units 58 and 143.

The control unit 452 is configured to be capable of acquiring information on a switching state of the first and second switching units 58 and 143. With this, the control unit 452 can determine from which of the first and second electric power supply units 59 and 14 the electric power is supplied, and can control the transmission and reception unit 453 to output identification information corresponding to a determination result.

Figure 8:
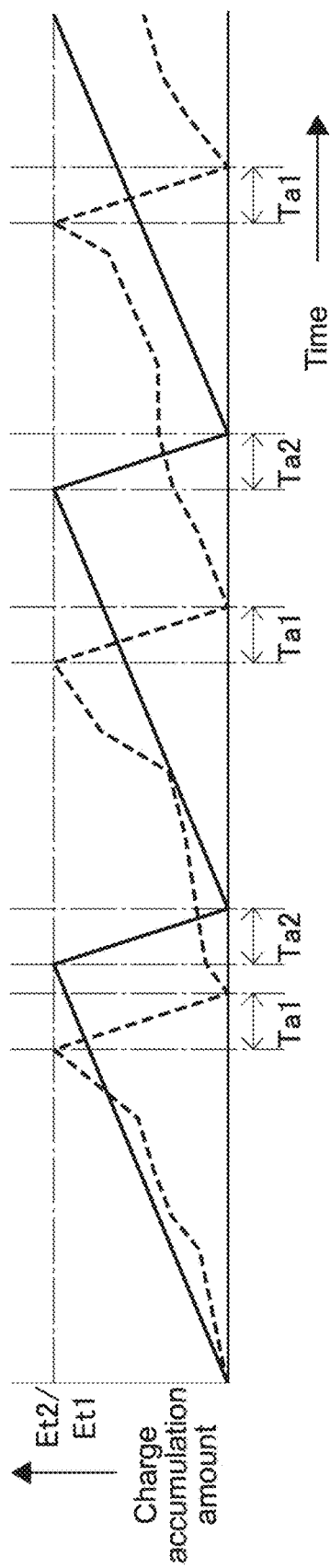
FIG. 8 is a graph showing charge accumulation amounts of a first power storage element and a second power storage element of the electronic apparatus according to the reference example.

FIG. 8 is a graph showing the charge accumulation amounts of the first power storage element 12 and the second power storage element 142 according to the reference example, in which the horizontal axis represents a time, and the vertical axis represents a charge accumulation amount. Referring to the figure, the operation of the electronic apparatus 5 will be described. Further, in the graph, a solid line represents the charge accumulation amount of the power storage element 142, and a broken line represents the charge accumulation amount of the power storage element 12.

Firstly, referring to the charge accumulation amount of the second power storage element 142 represented by the solid line, the charge accumulation amount is gradually increased by the power generation of the power generation element 141. When the charge accumulation amount of the second power storage element 142 then reaches a predetermined charge accumulation amount Et2, the switching unit 143 is switched from the blocking state to the conduction state, and the communication processing unit 55 is switched to the operating state accordingly. The communication processing unit 55 then outputs the identification information of the second electric power supply unit 14. The time in the operating state of the second electric power supply unit 14 is denoted by Ta2. In the operating state, the charge accumulation amount of the power storage element 142 is gradually lowered.

After the operating state of the second electric power supply unit 14 is terminated, the charge accumulation amount of the second power storage element 142 starts to increase again.

Meanwhile, referring to the charge accumulation amount of the first power storage element 12 represented by the broken line, the charge accumulation amount is gradually increased by the sensor 51. When the charge accumulation amount of the first power storage element 12 then reaches a predetermined charge accumulation amount Et1, the first switching unit 58 is switched from the blocking state to the conduction state, and the communication processing unit 55 is switched to the operating state accordingly. The charge accumulation amount Et1 may be identical to or different from the charge accumulation amount Et2. The communication processing unit 55 then outputs the identification information of the first electric power supply unit 59. The time in an operating state of the first electric power supply unit 59 is denoted by Ta1. In the operating state, the charge accumulation amount of the first power storage element 12 is gradually lowered.

After the operating state of the first electric power supply unit 59 is terminated, the charge accumulation amount of the first power storage element 12 starts to increase again.

In such a manner, according to the electronic apparatus 5, when both the first and second electric power supply units 39 and 14 reach a predetermined charge accumulation amount, the communication processing unit 55 is provided with electric power and then operated. Further, the communication processing unit 55 can output the identification information associated with the electric power supply unit to which electric power is supplied. Therefore, the electronic apparatus 5 can achieve electric power saving and output a variety of environment information. Further, with this, the external apparatus can estimate a power generation amount (charge accumulation amount) and the like in each of the electric power supply units 39 and 14 on the basis of operation intervals resulting from the electric power supply units 59 and 14. Note that, as described above, in both the solid line and the broken line, the charge accumulation amount may not be limited to zero at a point at which the charge accumulation amount starts to increase.

MODIFIED EXAMPLES

Hereinafter, modified examples of this embodiment will be described. In the following description, configurations similar to those of the electronic apparatus 1 will be denoted by identical reference signs and detailed descriptions thereof will be omitted.

Modified Example 1-1

For example, the electronic apparatus may include not a single sensor but a plurality of sensors.

Figure 9:
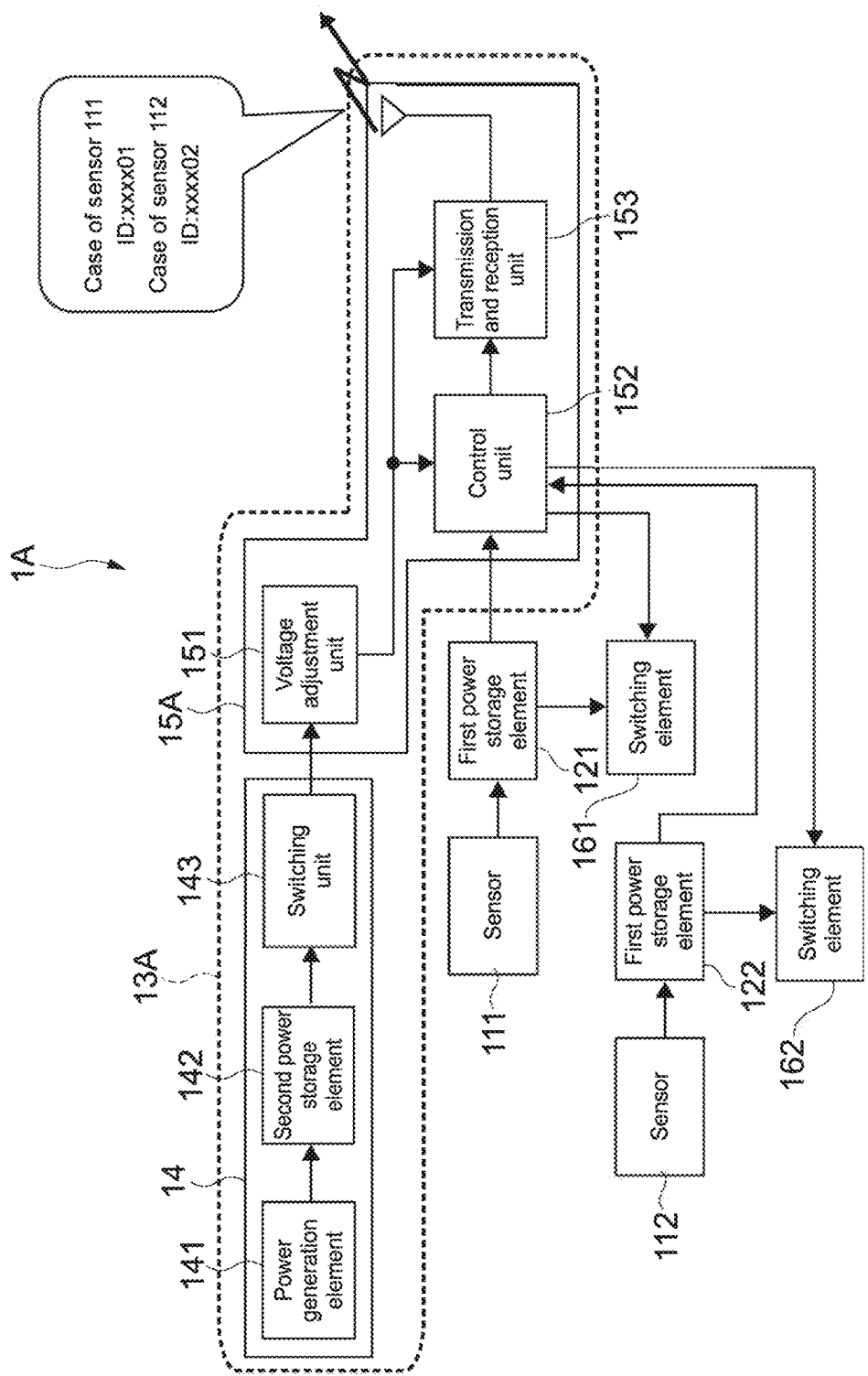
FIG. 9 is a block diagram showing a configuration of an electronic apparatus according to Modified Example 1-1.

FIG. 9 is a block diagram showing a configuration of an electronic apparatus 1A according to this modified example.

As shown in the figure, the electronic apparatus 1A includes a plurality of sensors 111 and 112 and a plurality of first power storage elements 121 and 122. The plurality of sensors 111 and 112 each generate charge in accordance with a surrounding environment. The plurality of first power storage elements 121 and 122 are respectively connected to the plurality of sensors 111 and 112 and respectively accumulate charge generated in those sensors 111 and 112. For example, the electronic apparatus 1A includes the two sensors 111 and 112, the two power storage elements 121 and 122, a communication module 13B, a switching element 161 connected to the power storage element 121, and a switching element 162 connected to the power storage element 122.

The sensor 111 and the sensor 112 each generate charge in accordance with a surrounding environment, similarly to the sensor 11, and for example, may respectively generate charge in accordance with different environments.

For example, the sensor 111 may generate charge in accordance with vibrations, and the sensor 112 may generate charge in accordance with a temperature difference. Alternatively, the sensor 111 may generate charge in accordance with vibrations, and the sensor 112 may generate charge in accordance with light irradiation.

Further, the power storage element 121 is connected to the sensor 111, and the power storage element 122 is connected to the sensor 112. The power storage elements 121 and 122 may be each a capacitor or another power storage element enumerated in the description of the power storage element 12. Further, the power storage elements 121 and 122 may have different configurations or an identical configuration.

The communication module 13A includes an electric power supply unit 14 and a communication processing unit 15A and is configured to be capable of outputting charge accumulation information of the power storage element 12, and the like.

The communication processing unit 15A is configured to be capable of acquiring the charge accumulation information from each of the plurality of power storage elements 121 and 122 and outputting the acquired pieces of accumulation information in the operating state.

With this, the electronic apparatus 1A can output a variety of environment information.

Furthermore, the communication processing unit 15A can output identification information of each of the plurality of sensors 111 and 112. The identification information of each of the plurality of sensors 111 and 112 is associated with the charge accumulation information, which is acquired from the power storage element 121 or 122 connected to a sensor identified by that identification information.

Further, those pieces of identification information may be each an identifier (ID; identification) formed of a predetermined character string. FIG. 9 shows examples of the identifier. In such a manner, the identifiers may include character strings (see in the figure) unique to the sensors 111 and 112.

With this, an external apparatus, which has received charge information, can easily determine to which of the sensors 111 and 112 the charge accumulation information correspond.

Modified Example 1-2

For example, the electronic apparatus may output, together with the charge accumulation information, time information associated with the charge accumulation information. In this case, the electronic apparatus can be configured as follows.

Figure 10:
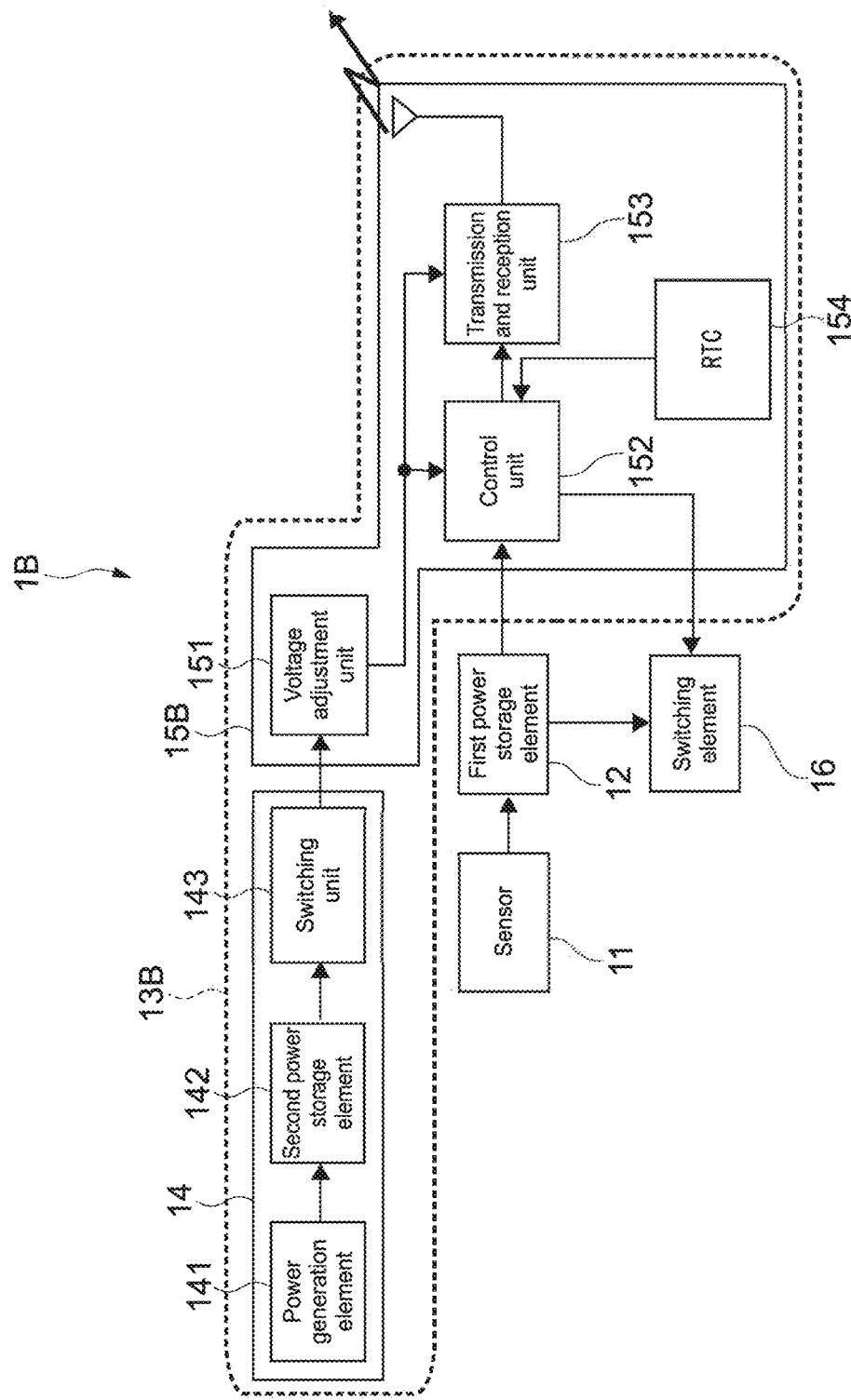
FIG. 10 is a block diagram showing a configuration of an electronic apparatus according to Modified Example 1-2.

FIG. 10 is a block diagram showing a configuration of an electronic apparatus 1B according to this modified example.

As shown in the figure, the electronic apparatus 1B includes a sensor 11, a power storage element 12, a communication module 13B, and a switching element 16.

The communication module 13B includes an electric power supply unit 14 and a communication processing unit 15B and is configured to be capable of outputting charge accumulation information of the power storage element 12, and the like.

The communication processing unit 15B includes a voltage adjustment unit 151, a control unit 152, a transmission and reception unit 153, and an RTC (Real Time Clock) 154 and is configured to be capable of outputting time information in addition to the charge accumulation information and the identifier.

The RTC 154 is connected to the control unit 152 and supplies time information to the control unit 152. The time information can be appropriately set as year/month/day, or the like. Alternatively, the control unit 152 may have a configuration incorporating the RTC.

Note that, although the illustration is omitted, the electronic apparatus 1 may be provided with a power supply apparatus for driving the RTC 154. The power supply apparatus is, for example, a secondary battery such as a lithium ion battery, a primary battery, or the like. The RTC 154 consumes little electric power. Therefore, a small battery such as a coin type battery may be used. Alternatively, electric power may be supplied to the RTC 154 by the electric power supply unit 14.

The control unit 152 supplies, in response to switching from the stand-by state to the operating state, the charge accumulation information and the time information to the transmission and reception unit 153. The transmission and reception unit 153 outputs the charge accumulation information and the time information to an external apparatus. Note that the transmission and reception unit 153 may output the identification information of the sensor 11 in addition to those pieces of information.

With the configuration as described above, the electronic apparatus 1 can output the time information and facilitate a temporal information analysis by the external apparatus.

Modified Example 1-3

For example, the electric power supply unit may have a configuration including no switching unit.

Figure 11:
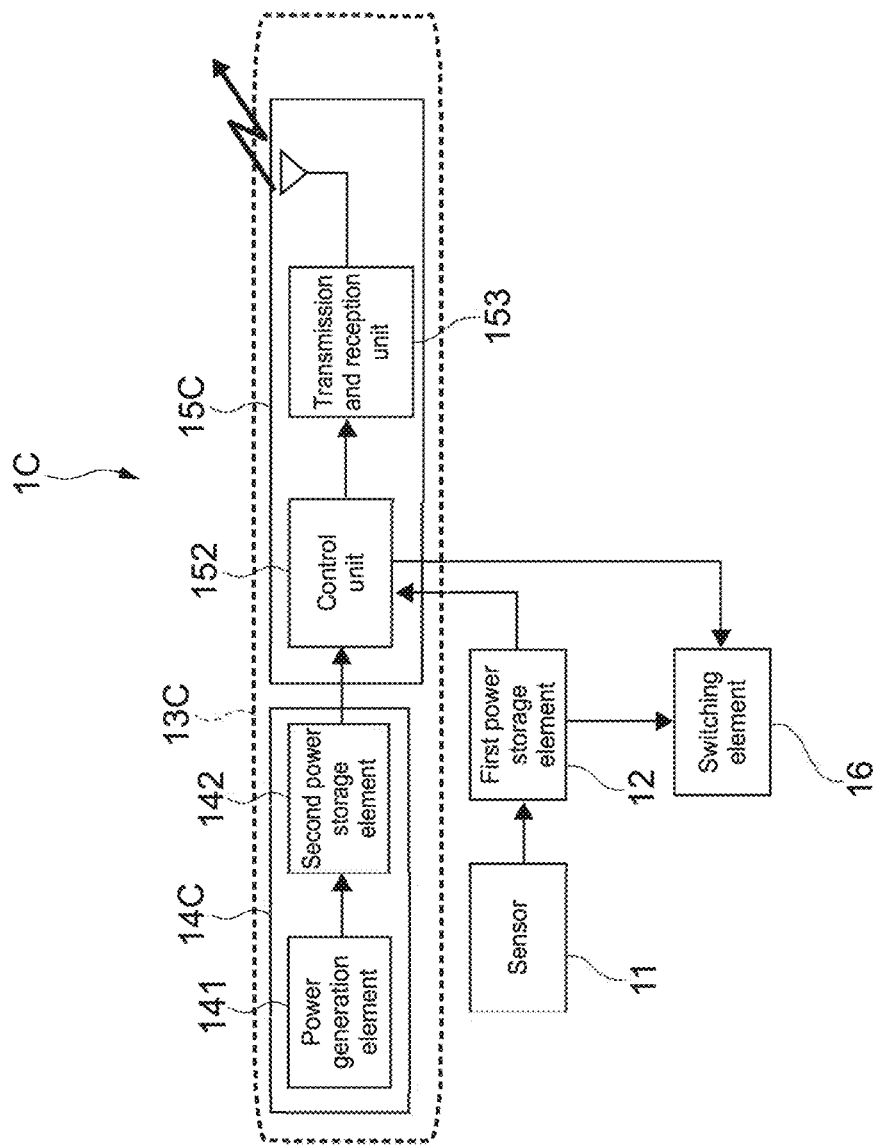
FIG. 11 is a block diagram showing a configuration of an electronic apparatus according to Modified Example 1-3.

FIG. 11 is a block diagram showing a configuration of an electronic apparatus 1C according to this modified example.

As shown in the figure, the electronic apparatus 1C includes a sensor 11, a power storage element 12, a communication module 13C, and a switching element 16.

The communication module 13C includes an electric power supply unit 14C and a communication processing unit 15C and is configured to be capable of outputting charge accumulation information of the power storage element 12, and the like.

The electric power supply unit 14C includes a power generation element 141 and a second power storage element 142 and does not include a switching unit.

The communication processing unit 15C is configured to be capable of being switched between a stand-by state and an operating state on the basis of the electric power supplied from the electric power supply unit 14. The communication processing unit 15C is configured to be capable of acquiring charge accumulation information from the power storage element 12 and outputting the accumulation information in the operating state. In this modified example, the communication processing unit 15C determines whether to switch between the stand-by state and the operating state on the basis of the electric power supplied from the electric power supply unit 14 (e.g., a voltage value of the second power storage element 142). With this, the communication processing unit 15C can be switched to the operating state without using the switching unit, in accordance with an electric power condition from the electric power supply unit 14.

In this case, the electronic apparatus 1 may be provided with a power supply apparatus for driving or assisting in driving the communication processing unit 15C. The power supply apparatus is, for example, a secondary battery such as a lithium ion battery, a primary battery, or the like. If little electric power is consumed, a small battery such as a coin type battery may be used. Alternatively, electric power may be supplied to the communication processing unit 15C by the electric power supply unit 14C.

Further, as shown in the figure, the communication processing unit 15C may have a configuration including no voltage adjustment unit. In this case, the communication processing unit 15C may have a configuration in which, for example, the control unit 152 includes a voltage adjustment circuit or the like.

The electronic apparatus 1C having such a configuration can also acquire and transmit information on a change in surrounding environment in the stand-by state.

Modified Example 1-4

For another modified example, the electronic apparatus may include an energy storage element in which switching between a storage state and a release state of kinetic energy can be performed.

Figure 12:
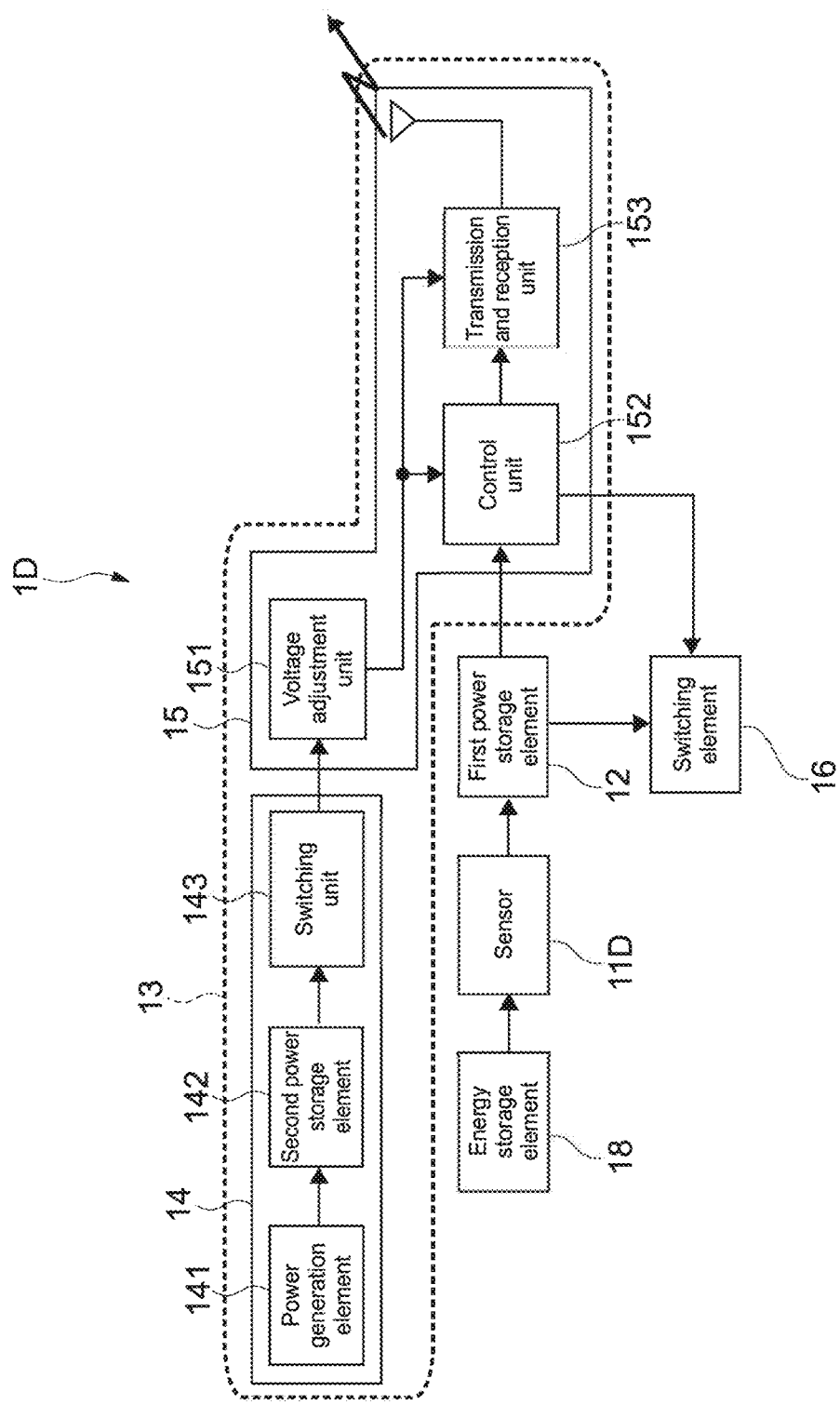
FIG. 12 is a block diagram showing a configuration of an electronic apparatus according to Modified Example 1-4.

FIG. 12 is a block diagram showing a configuration of an electronic apparatus 1D according to this modified example.

As shown in the figure, the electronic apparatus 1D includes a sensor 11D, a power storage element 12, a communication module 13, a switching element 16, and an energy storage element 18.

Examples of the energy storage element 18 can include a small spiral spring configured as a microelectromechanical (MEMS) element. The energy storage element 18 is configured to be capable of accumulating kinetic energy in accordance with a surrounding environment, such as vibrations.

The sensor 11D is connected to the energy storage element 18 and includes a mechanism that generates electric power using electromagnetic induction. Specifically, the sensor 11D includes, for example, a magnet and a coil and is configured such that the magnet can be displaced with respect to the coil. With this, the sensor 11D is capable of driving the magnet in accordance with kinetic energy supplied from the energy storage element 18 and generating charge.

With such a configuration as well, the sensor 11D is configured to be capable of generating charge in accordance with a surrounding environment, and the electronic apparatus 1D can output charge accumulation information.

Further, the electric power supply unit of the communication module may include an energy storage element (not shown). In this case, the energy storage element may be connected to the power generation element, and the power generation element may include a mechanism that generates electric power using electromagnetic induction.

Modified Example 1-5

For another modified example, the electronic apparatus may include a heat storage element that accumulates thermal energy and provides the thermal energy to the sensor.

Figure 13:
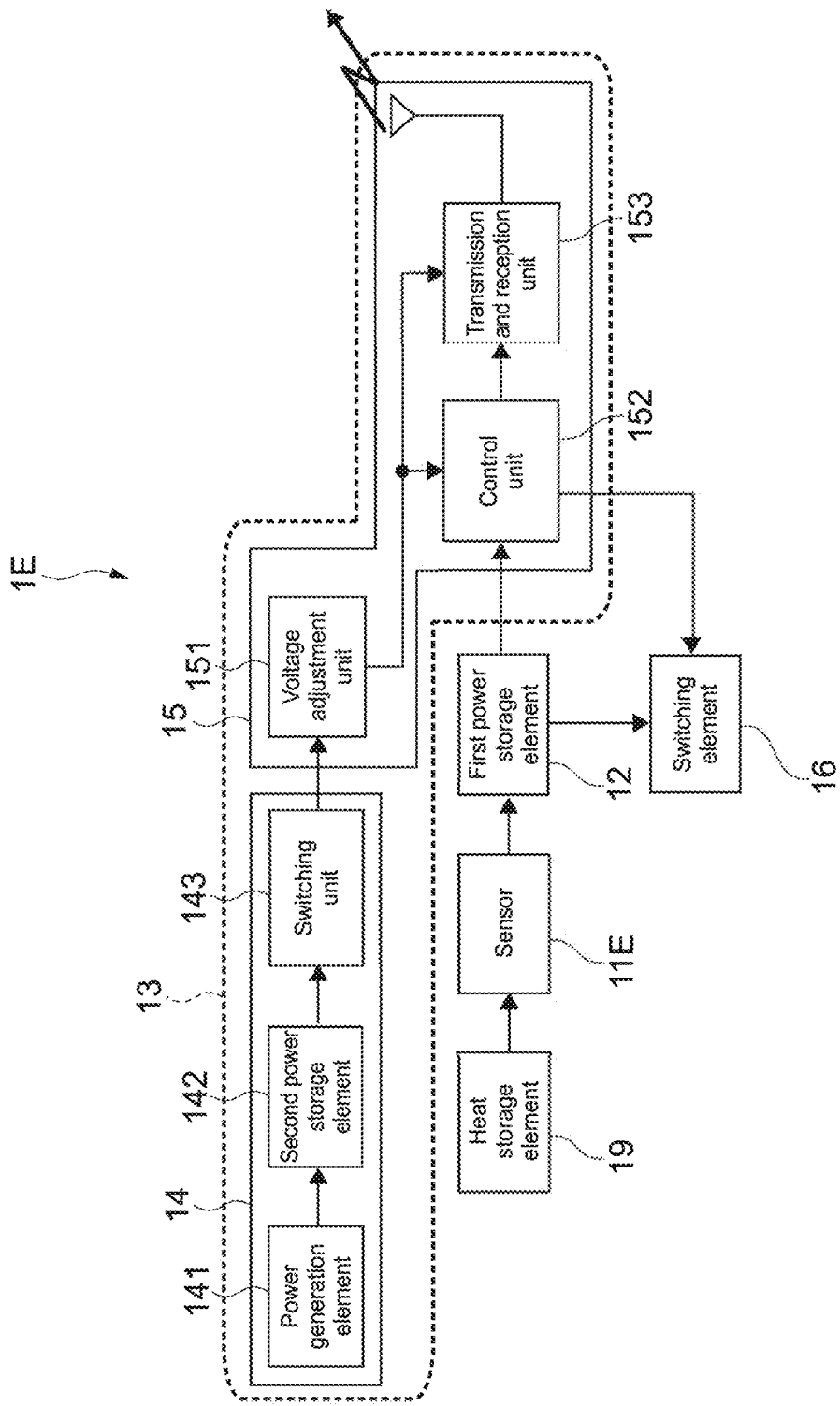
FIG. 13 is a block diagram showing a configuration of an electronic apparatus according to Modified Example 1-5.

FIG. 13 is a block diagram showing a configuration of an electronic apparatus 1E according to this modified example.

As shown in the figure, the electronic apparatus 1E includes a sensor 11E, a power storage element 12, a communication module 13, a switching element 16, and a heat storage element 19.

In this case, the sensor 11E is configured to be capable of converting thermal energy, which is stored in the heat storage element 19, into electric energy, to generate charge.

With such a configuration as well, the electronic apparatus 1E can output accumulation information of charge generated in accordance with a surrounding environment of the sensor 11E.

Further, the electric power supply unit of the communication module may include a heat storage element (not shown). In this case, the heat storage element may be connected to the power generation element and the switching unit, and the switching unit may be constituted of, for example, a switch in which the conduction state can be provided by switching of a contact. For example, the switch may include bi-metal deformable due to thermal energy. With this, electric power can be supplied to the communication processing unit via the above switching unit.

Modified Example 1-6

The first power storage element may include a secondary battery, in addition to the capacitor or instead of the capacitor.

For example, the first power storage element may include a capacitor and a secondary battery and may be configured such that the secondary battery is charged in accordance with charge generated by the sensor, and the capacitor stores electric power in accordance with output electric power from the charged secondary battery.

In this case, the first power storage element may further include, in addition to the capacitor and the secondary battery, a charger (charging circuit) that charges the secondary battery, a regulator IC that adjusts a voltage input to the charger, and a capacitor for driving the charger. Further, the first power storage element may include, for example, a battery for driving the charger, instead of the capacitor for driving the charger.

Alternatively, the first power storage element may have a configuration in which the secondary battery and the switching unit are directly connected without providing a capacitor. In this case, the communication processing unit can acquire a voltage value of the secondary battery as charge accumulation information.

Further, the second power storage element of the electric power supply unit may similarly include a secondary battery in addition to the capacitor or instead of the capacitor.

Modified Example 1-7

Further, the "predetermined electric power", which is a reference of switching of the switching unit 143, is not limited to electric power that is equal to or larger than electric power with which the communication processing unit 15 can be operated. The "predetermined electric power" may be electric power smaller than electric power with which the communication processing unit 15 is operable. In this case, the electronic apparatus 1 may be provided with a power supply apparatus for assisting in driving the communication processing unit 15.

Modified Example 1-8

The casing is not limited to the configuration shown in FIG. 1 and may have a configuration corresponding to an attachment mode or the like.

For example, the casing may not include a tab and a hinge and may be formed of only a main body. Further, the main body may be formed in a disk shape as a whole.

Furthermore, the casing may not include a hole portion and may include, for example, an attachment tool connected to a part of the main body. This attachment tool may include, for example, a chain or may include a chain and a key ring connected the chain. Further, the casing may include a pin that can be fixed to fabric and may be formed in a tin badge shape as a whole.

With this, the casing can be attached to a bag, an ID card case, a collar of an animal, and the like.

Second Embodiment

An information processing system using the electronic apparatus 1 described in the first embodiment will be described as a second embodiment. Note that in the following description configurations similar to those of the first embodiment will be denoted by identical reference signs and detailed descriptions thereof will be omitted.

[Configuration of Information Processing System]

Figure 14:
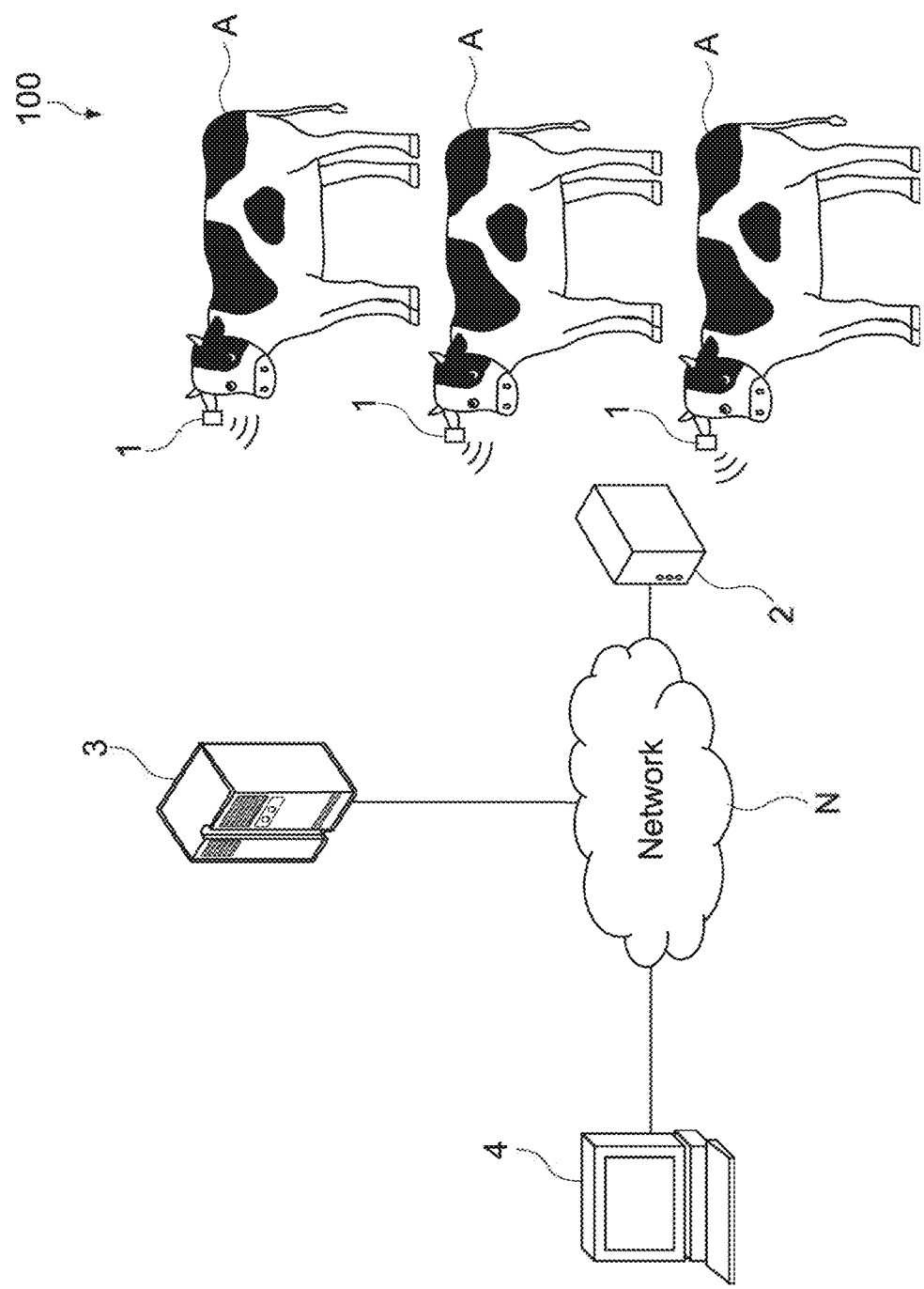
FIG. 14 is a schematic diagram showing a schematic configuration of an information processing system according to a second embodiment of the present technology.

FIG. 14 is a schematic diagram showing a schematic configuration of an information processing system according to this embodiment.

As shown in the figure, an information processing system 100 includes a plurality of electronic apparatuses 1, a communication apparatus 2, and a processing apparatus 3.

For example, the information processing system 100 is a system introduced into, for example, a stockbreeding facility. The processing apparatus 3 is configured to be capable of acquiring predetermined information from the electronic apparatus 1 attached to each livestock animal A and generating information on a surrounding environment of the electronic apparatus 1.

Examples of the livestock animals can include beef cattle, cows, pigs, horses, sheep, goats, and poultry that are industrial animals and dogs, cats, and rabbits that are pets. Hereinafter, beef cattle will be taken as an example.

Although the stockbreeding facility is not particularly limited as long as the above-mentioned livestock animals can be accommodated, and includes a barn and a pasture, for example.

As shown in FIG. 14, the plurality of electronic apparatuses 1 are respectively attachable to a plurality of livestock animals A. For example, each electronic apparatus 1 is attached to an ear of each livestock animal A. Note that the attachment position is not limited to the ear and it may be a neck, a back, a leg, or the like. However, it is more favorable to attach the electronic apparatus 1 to the ear rather than the neck or leg for the purpose of lowering the possibility that the electronic apparatus 1 may be detached due to behavior of the livestock animal A to rub itself against a fence or the like or its collision with another livestock animal.

The communication apparatus 2 receives information output from the electronic apparatus 1 and transmits the received information to the processing apparatus 3 on a network N. The network N can be, for example, the Internet, a local area network, or the like. As shown in the figure, the communication apparatus 2 may be attached to, for example, a gate or the like of the stockbreeding facility. Alternatively, the communication apparatus 2 may be configured to be attachable or portable and may be carried by working staff or the like of the stockbreeding facility.

The processing apparatus 3 is a server apparatus on the network N and receives predetermined information from the electronic apparatus 1, which has been transmitted through the communication apparatus 2. The processing apparatus 3 is, for example, configured as an information processing apparatus.

The information processing system 100 may be further connected to an external apparatus 4 via the network N.

Figure 15:
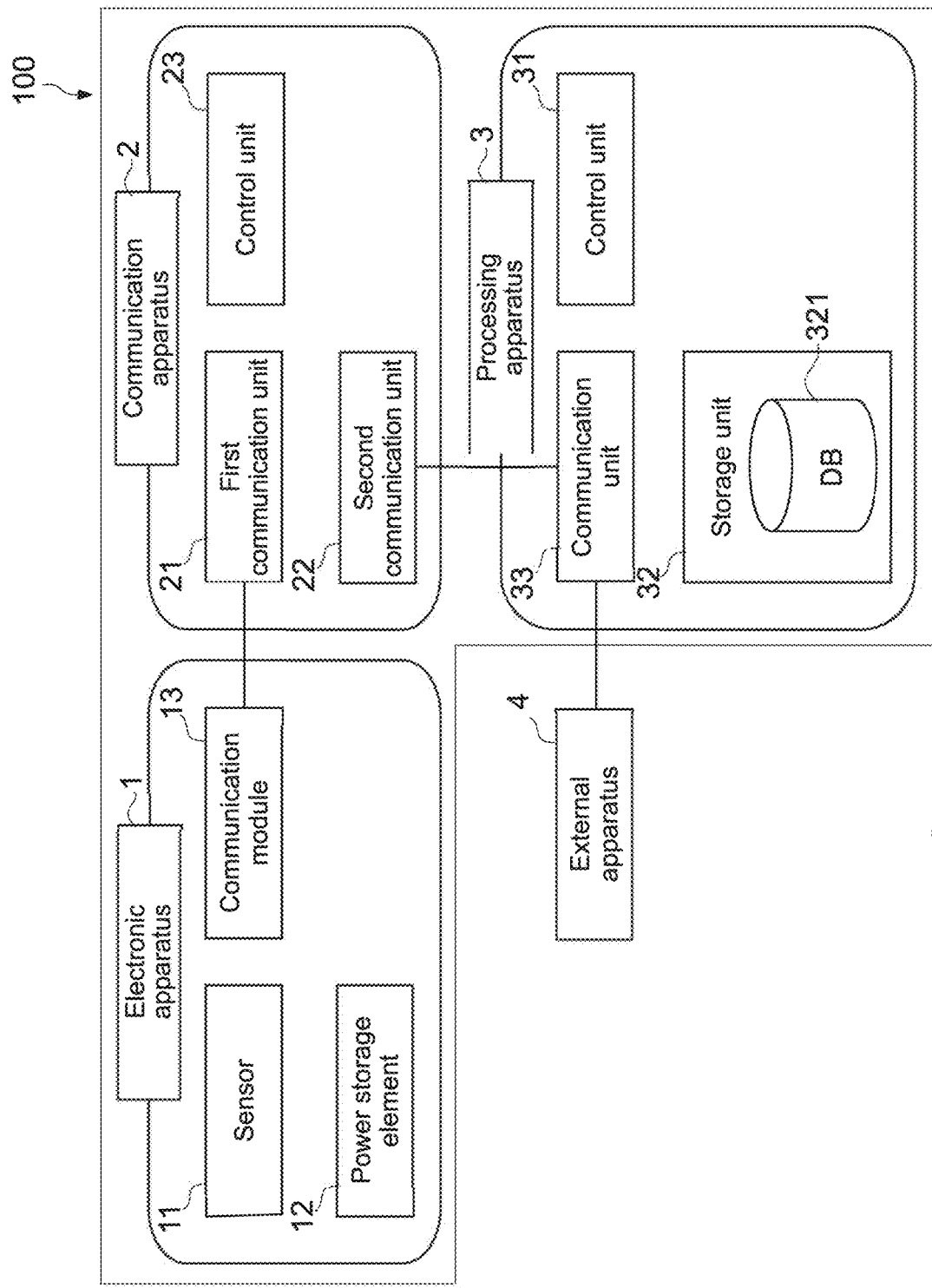
FIG. 15 is a block diagram showing a configuration of each apparatus included in the information processing system.

FIG. 15 is a block diagram showing configurations of the respective apparatuses included in the information processing system 100. Referring to the figure, a configuration of each apparatus will be described.

Note that the electronic apparatus 1 can apply the configuration described in the first embodiment, and thus detailed description thereof will be omitted.

(Communication Apparatus)

The communication apparatus 2 is configured to be capable of communicating with each of the communication module 13 of the electronic apparatus 1 and a communication unit 33 of the processing apparatus 3 and transmitting, to the communication unit 33, charge accumulation information and the like output from the communication module 13. Further, although only the electronic apparatus 1 is shown in FIG. 15, the communication apparatus 2 can be configured to be capable of communicating with a plurality of electronic apparatuses.

As shown in FIG. 15, the communication apparatus 2 includes a first communication unit 21, a second communication unit 22, and a control unit 23.

The first communication unit 21 is configured to be capable of communicating with the communication module 13 of the electronic apparatus 1. The first communication unit 21 has a configuration capable of performing, for example, communication utilizing electromagnetic waves (including infrared rays), wireless communication such as communication utilizing an electric field, or communication with wires.

The second communication unit 22 is configured to be capable of connecting to the network N and communicating with the processing apparatus 3. Specifically, the second communication unit 22 is capable of connecting to the network N and communicating with the processing apparatus 3 by using a wireless LAN (IEEE802.11, etc.) such as WiFi (Wireless Fidelity) and a 3G or 4G network for mobile communication.

The control unit 23 controls the first communication unit 21 and the second communication unit 22 and is, for example, realized by a processor such as a CPU and memories such as a RAM and a ROM.

(Processing Apparatus)

As shown in FIG. 15, the processing apparatus 3 includes a control unit 31, a storage unit 32, and the communication unit 33. The processing apparatus 3 may include one or more servers.

The control unit 31 is realized by, for example, a processor such as a CPU and memories such as a RAM and a ROM, and generates information on a surrounding environment of the electronic apparatus 1 on the basis of output accumulation information.

The storage unit 32 includes, for example, an HDD (Hard Disk Drive) and a nonvolatile memory such as a flash memory (SSD; Solid State Drive). With this, the storage unit 32 can store a database 321 on environment information corresponding to each livestock animal A to which the electronic apparatus 1 is attached.

The communication unit 33 is configured to be capable of connecting to the Internet N and communicating with the communication apparatus 2 and the external apparatus 4.

Specifically, the communication unit 33 hay have a configuration capable of performing communication with wires using an NIC (Network Interface Card) for Ethernet (registered trademark) or wireless communication using a wireless LAN (IEEE802.11, etc.) such as WiFi (Wireless Fidelity) and a 3G or 4G network for mobile communication.

The management apparatus 3 may include configurations such as an input device, a display device, and a speaker besides the above-mentioned configurations in a manner that depends on needs, though not shown in the figure.

The external apparatus 4 to which the processing apparatus 3 is connected may be, for example, a master monitor apparatus that controls a gate of a stockbreeding facility, an automatic feeder, a monitoring device, or the like. Alternatively, the external apparatus 4 may be a PC (Personal Computer), a smartphone, a tablet terminal, or the like of a user who manages the stockbreeding facility or the like.

The processing apparatus 3 is configured to be capable of generating information (environment information) on a surrounding environment of the electronic apparatus 1 on the basis of output accumulation information.

The environment information may be, for example, information on behavior of a human or animal to which the electronic apparatus 1 is attached, or information on a state of a human or animal to which the electronic apparatus 1 is attached. Alternatively, the environment information may be information on the weather around the electronic apparatus 1 and the like.

Examples of the information on behavior of a human or animal include an activity amount, a staying place, and an action of a human or animal.

Examples of the information on a state of a human or animal include the presence/absence of fever, a reproductive cycle (estrus of animal etc.), and meat quality of a livestock animal.

Examples of the information on the weather around the electronic apparatus 1 include temperature and weather.

Those pieces of environment information can be generated from the accumulation information as follows, for example.

(Example of Generating Environment Information 1: Case where Sensor Generates Charge by Vibrations)

The control unit 31 of the processing apparatus 3 can generate information on an activity amount of a human or an animal on the basis of charge accumulation information of the electronic apparatus 1 that generates charge by vibrations. For example, it can be estimated that, out of two livestock animals, one that has a larger charge accumulation amount in the electronic apparatus 1 attached thereto has a larger activity amount.

The control unit 31 of the processing apparatus 3 can also generate information on an action or move of a human or an animal. For example, a move of the neck (head) and a move of a limb are different in vibration frequency. Therefore, those moves are also different in charge accumulation pattern. Thus, their actions can be identified. Further, if a characteristic charge accumulation pattern can also be found in walking, running, mounting of livestock animals, or the like, their actions can be estimated.

(Example of Generating Environment Information 2: Case where Sensor Generates Charge by Light Irradiation)

The control unit 31 of the processing apparatus 3 can generate information on a staying place of a human or an animal on the basis of charge accumulation information of the electronic apparatus 1 that generates charge by light irradiation. For example, the control unit 31 can estimate situations of staying outdoors and indoors.

The control unit 31 of the processing apparatus 3 can also generate information on the weather around the electronic apparatus 1. For example, the control unit 31 can estimate fine weather if the output charge accumulation amount is a predetermined threshold or more, and can estimate cloudy weather or rainy weather if the output charge accumulation amount is less than a predetermined threshold. Further, the control unit 31 can estimate sunshine duration.

(Example of Generating Environment Information 3: Case where Sensor Generates Charge by Temperature Difference)

The control unit 31 of the processing apparatus 3 can generate information on temperature around the electronic apparatus 1 on the basis of charge accumulation information of the electronic apparatus 1 that generates charge in accordance with a temperature difference. For example, the control unit 31 can assume that a body temperature of a human body or animal to which the electronic apparatus 1 is attached is substantially constant, and can estimate temperature from a temperature difference between the body temperature and an ambient temperature.

The control unit 31 of the processing apparatus 3 can also generate information on the presence/absence of fever of a human or an animal. In this case, the control unit 31 can estimate that a target human or animal has a fever, for example, because the charge accumulation amount output from the sensor 11 of the target human or animal is larger than that of other humans or animals in a similar staying place.

(Example of Generating Environment Information 4: Case where Sensor Generates Charge by Radio Waves)

The control unit 31 of the processing apparatus 3 can generate information on a distance from a radio wave generation source or the like on the basis of the charge accumulation information of the electronic apparatus 1 that generates charge by radio waves and can also estimate a staying place.

(Example of Generating Environment Information 5: Case where Electronic Apparatus Includes Plurality of Sensors)

If the electronic apparatus 1 includes a plurality of sensors 11, the control unit 31 can take into account, for example, in addition to the information on the fact that a target human or animal has a fever, information on behavior and a staying place thereof. With this, the control unit 31 can generate a more variety of information such as the presence/absence of a load of sickness or stress or whether the livestock animal is in the breeding season or not.

Further, if the electronic apparatus 1 includes a plurality of sensors 11, the control unit 31 can also estimate meat quality of livestock animals on the basis of pieces of accumulation information from those sensors 11. It is considered that the meat quality of livestock animals generally depends on an activity amount (exercise load), the presence/absence of stress, feed, and the like. As described above, the control unit 31 can acquire accumulation information, and can thus estimate the information on an activity amount, the presence/absence of stress, and the like. Furthermore, since the control unit 31 can estimate grasses and the like eaten by those livestock animals as feed on the basis of a staying place, the meat quality can also be estimated.

[Operation Example of Processing Apparatus]

Figure 16:
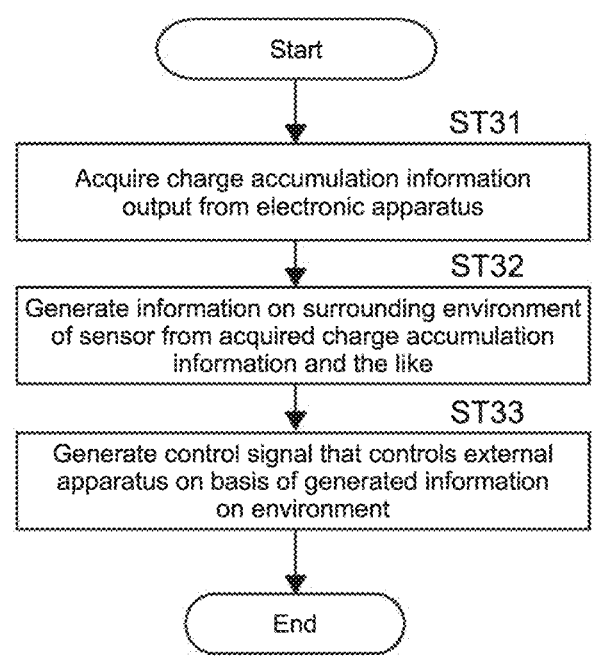
FIG. 16 is a flowchart showing an operation example of a processing apparatus included in the information processing system.

FIG. 16 is a flowchart showing an operation example of the processing apparatus. In the figure, it is assumed that the operation subject is the control unit 31 of the processing apparatus 3.

Firstly, the control unit 31 acquires charge accumulation information output from the electronic apparatus 1, which is attached to a human or an animal (e.g., livestock animal A) (ST31). More specifically, the control unit 31 can acquire charge accumulation information and an identifier that are received by the communication unit 33 via the communication apparatus 2.

Subsequently, the control unit 31 generates information (environment information) on a surrounding environment of the sensor 11 of the electronic apparatus 1 from the acquired charge accumulation information and the like (ST32). In this operation example, the control unit 31 generates surrounding environment information of a human or an animal to which the electronic apparatus 1 is attached.

Specifically, the control unit 31 can generate environment information by using a predetermined algorithm. This algorithm may be generated by, for example, machine learning using data set constituted of charge accumulation information and real environment information corresponding thereto, and may be configured to be capable of estimating the surrounding environment on the basis of the charge accumulation information. With this, environment information with high reliability can be generated. Alternatively, the algorithm is not limited to one generated by machine learning, and may be configured to be capable of analyzing surrounding environment of a human or animal to which the electronic apparatus 1 is attached on the basis of charge accumulation information.

Further, the control unit 31 can generate, in this step, a plurality of pieces of environment information. For example, if the sensor 11 generates charge by vibrations, the control unit 31 can generate information on both an activity amount and an action as described above. Further, if the electronic apparatus 1 includes a plurality of sensors 11, the control unit 31 can generate a variety of environment information such as an activity amount and weather, and an activity amount and a staying place.

Subsequently, the control unit 31 generates a control signal that controls the external apparatus 4 on the basis of the generated environment information (ST33).

For example, if the control unit 31 estimates that an activity amount of a certain livestock animal is smaller than that of another livestock animal, the control unit 31 can generate a control signal including this information. With this, the external apparatus 4 can control a gate so as to prolong an open time of the gate of a stall of a barn to which that livestock animal belongs on the basis of this control signal.

Alternatively, if the control unit 31 estimates a staying place of a certain livestock animal in a grazing land, the control unit 31 can generate a control signal including this information. With this, the external apparatus 4 can control an automatic feeder to compound a feed that can compensate for nutrient balance of the livestock animal in view of vegetation or the like of the estimated staying place and supply the feed.

Further, the control unit 31 can also generate a control signal for causing a display device or the like of the external apparatus 4 to, for example, display identification information of the electronic apparatus 1 (sensor 11) attached to a human or an animal and the generated environment information.

Lastly, the control unit 31 controls the communication unit 33 to output the generated control signal (ST34).

In such a manner, the processing apparatus 3 acquires the charge accumulation information from the electronic apparatus 1 and can thus acquire information on a surrounding environment of a human or an animal. With this, power consumption of the electronic apparatus 1 can be suppressed. Therefore, it is possible to save troubles in maintenance such as disposal of the electronic apparatus 1, replacement of the battery, and charging.

Further, the processing apparatus 3 acquires the charge accumulation information from the electronic apparatus 1 and can thus easily grasp a health state of a human or an animal or determine the breeding season, for example. With this, if the information processing apparatus 100 is introduced into the stockbreeding facility, individual livestock animals can be easily managed.

Furthermore, the control unit 31 of the processing apparatus 3 can generate a control signal on the basis of environment information. Therefore, it is possible to cause also the external apparatus 41 to execute control conforming to the environment information. For example, if the information processing apparatus 100 is introduced into the stockbreeding facility, another device introduced into the stockbreeding facility can be caused to execute control conforming to the environment information. A large-scale livestock raiser or a livestock raiser that performs grazing relatively difficult to manage can also suitably and easily manage individual livestock animals.

Further, the processing apparatus 3 can automatically receive information from the plurality of electronic apparatuses 1 and easily acquire the charge accumulation information from the plurality of electronic apparatuses 1 in a lump. With this, a trouble in manually collecting data for each of the electronic apparatuses 1 can be saved.

MODIFIED EXAMPLES

Modified examples of the information processing system 100 will be described.

Modified Example 2-1: Acquisition of Information on Position

The control unit 31 may acquire information on a position of the electronic apparatus 1 on the basis of the output of the electronic apparatus 1. The information on a position used herein includes information on at least one of a distance of the electronic apparatus 1 from a reference position and a direction of the electronic apparatus 1 when viewed from the reference position. The reference position can be a position of the communication apparatus 2, for example.

In this modified example, the communication apparatus 2 can generate information on a position of the electronic apparatus 1 with the position of the communication apparatus 2 being as a reference, and can perform processing of associating this information with the charge accumulation information output from the electronic apparatus 1.

A method of acquiring the information on a position by the control unit 31 is not particularly limited.

For example, it is known that there is a correlation between a signal strength of communication data and a communication distance. In this regard, the communication apparatus 2 can transmit information on the signal strength from the electronic apparatus 1, to the processing apparatus 3 together with the charge accumulation information and the like. Specifically, when outputting the received accumulation information, the communication apparatus 2 can output this information in association with the information on the signal strength. With this, the control unit 31 can acquire the information on the distance of the electronic apparatus 1 from the communication apparatus 2.

Alternatively, the first communication unit 21 of the communication apparatus 2 includes an antenna. By mechanically or electrically changing the directivity of the antenna, the communication apparatus 2 is acquire information on a direction of each electronic apparatus 1 when viewed from the communication apparatus 2 and can transmit it to the processing apparatus 3.

Further, the electronic apparatus 1 may include a GPS communication unit (not shown) so as to be capable of outputting position information. In this case, the electronic apparatus 1 may be provided with a power supply unit for driving the GPS communication unit.

Modified Example 2-2: Chronological Generation of Environment Information

By chronologically processing the generated environment information, the control unit 31 can estimate a state of a human or an animal to which the electronic apparatus 1 is attached within a predetermined period.

For example, the electronic apparatus 1 may output, together with charge accumulation information, time information associated with that accumulation information. In this case, as described in Modified Example 1-2 described above, the electronic apparatus 1 may include an RTC.

Alternatively, the control unit 31 may include the RTC or may be connected to the RTC, to perform processing of associating the time information with the received charge accumulation information.

Further, the control unit 23 of the communication apparatus 2 may include an RTC or may be connected to the RTC, to perform processing of associating the time information with the received charge accumulation information.

Modified Example 2-3: Generation of API

In the above-mentioned embodiment, the example in which the control unit 31 generates the control signal for controlling the external apparatus from the generated environment information has been described. However, the generated environment information can be utilized in the following manner.

That is, the control unit 31 may process the environment information generated by using an algorithm and generate an API (Application Programming Interface) utilized by software installed in the external apparatus or the like.

For example, if the generated environment information is information on the meat quality or health state of the livestock animal, the above-mentioned software can be a part of a loan amount determination application program or the like for determining a loan amount to the livestock raiser. Alternatively, the above-mentioned software can be one that provides the program or the like with data. The generated environment information in this case can be meat quality of a livestock animal involved with the loan amount, the health state of the livestock animal, and the like.

With this, the generated environment information can be effectively utilized.

Modified Example 2-4: Determination and Notification of Human or Animal Satisfying Predetermined Condition For example, the control unit 31 may be configured to generate environment information on behavior or health states of a plurality of humans or animals on the basis of charge accumulation information and determine a human or animal satisfying a predetermined condition, out of the plurality of humans or animals.

For example, the control unit 31 can estimate whether each of the plurality of livestock animals is in estrus on the basis of the charge accumulation information and determine a livestock animal estimated as one being in estrus. In this case, the control unit 31 can determine a livestock animal by using acquired identification information of each sensor.

Furthermore, the control unit 31 can generate a control signal including information on the determined human or animal and the identification information of the sensor attached to the determined human or animal. When the control signal is transmitted to an external apparatus having a notification function, it is possible to notify a user of the external apparatus of the human or animal satisfying a predetermined condition.

Modified Example 2-5: Utilization of Information on Power Generation Amount of Power Generation Element The control unit 31 can generate information on a surrounding environment of the electronic apparatus 1, in addition to the charge accumulation information, in consideration of the number of receptions from the electronic apparatus 1 or a reception frequency.

The output of the electronic apparatus 1 is executed when electric power supply from the electric power supply unit 14 satisfies a predetermined condition, that is, when the power generation amount of the power generation element 141 is a predetermined power generation amount or more. Therefore, the control unit 31 can acquire information on a power generation amount of the power generation element 141 on the basis of the number of receptions from the electronic apparatus 1 or a reception frequency, and can generate environment information similarly to the charge accumulation information.

The control unit 31 generates environment information on the basis of both of the charge accumulation information and the information on the number of receptions from the electronic apparatus 1. Therefore, the control unit 31 can generate environment information on the presence/absence of a load of sickness or stress, or on the meat quality of a livestock animal as described in "Example of Generating Environment Information 5 (Case Where Electronic Apparatus Includes Plurality of Sensors)". Further, the control unit 31 can also generate different pieces of environment information.

Modified Example 2-6: Output Adjustment (Calibration) of Electronic Apparatus The processing apparatus 3 can adjust charge accumulation information acquired from the electronic apparatus 1. The "adjustment" used herein may be, for example, calibration. For example, the processing apparatus 3 may statistically process accumulation information from the plurality of electronic apparatuses 1, to calibrate the output of one electronic apparatus 1 or may statistically process chronological charge accumulation information or the like from one electronic apparatus 1, to adjust the output of that electronic apparatus 1.

In output characteristics of the sensors of the electronic apparatus 1, there are considerable individual differences at the manufacturing stage or considerable individual differences due to changes over years which are caused by usage. Regarding this individual difference, data on an identical individual may be continuously acquired, a relative amount change thereof may be handled as information, and thus the individual difference may be cancelled. Alternatively, for example, a plurality of humans or animals may be exposed to the same environment and calibration may be performed on the basis of differences in charge accumulation amount under the same environment. That is, for example, humans or animals are exposed to an area of the same light source, an area of the same vibration, an area of the same radio field intensity, and an area of the same temperature. Calibration may be performed by making the output of the respective sensors at this time uniform. Further, by setting normality/abnormality thresholds with respect to the output of the sensor at this time in advance, an abnormality of the electronic apparatus or an abnormality of the sensor may be detected and used as maintenance information. Note that the area of the same environment may be, for example, set on a path through which a human or animal passes or may be a space that is not the path. Furthermore, a uniform environment space may be formed by controlling a temperature/humidity/illuminance controller of a space in which humans or animals normally stay. A dedicated space may be used for forming a more stable environment space.

Output adjustment (calibration) of the electronic apparatus 1 by the processing apparatus 3 may be performed simultaneously with the generation processing of the environment information or may be performed separately from that processing. If such output adjustment is performed separately from the generation processing of the environment information, the processing apparatus 3 can perform output adjustment at a timing corresponding to a user's input operation, for example.

Modified Example 2-7: Modified Example of Information Processing System

The information processing system may have a configuration including no communication apparatus.

Figure 17:
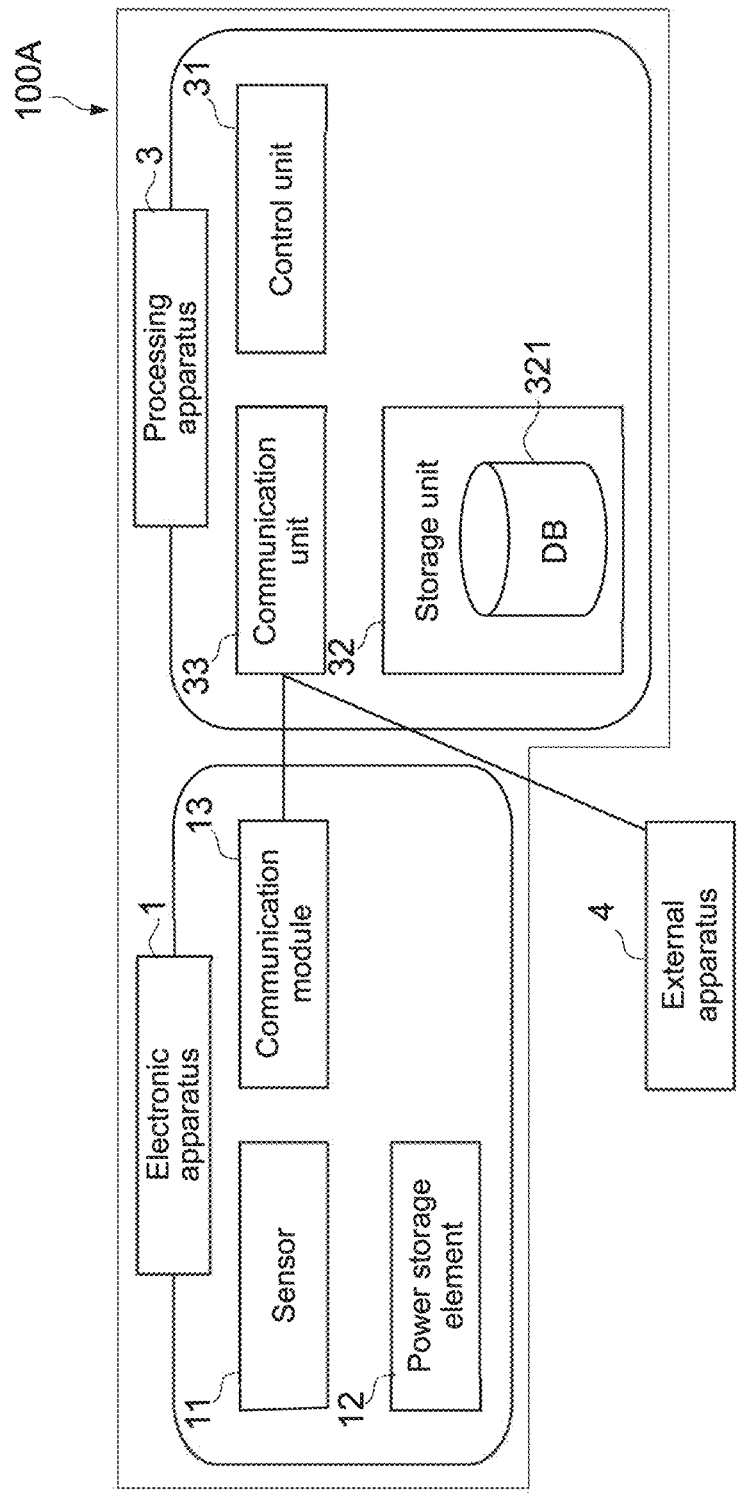
FIG. 17 is a block diagram showing a configuration of an information processing system according to Modified Example 2-7.

FIG. 17 is a block diagram showing a configuration of an information processing system 100A according to this modified example.

As shown in the figure, the information processing system 100A includes an electronic apparatus 1 and a processing apparatus 3 but does not include a communication apparatus. That is, a communication module 13 of the electronic apparatus 1 includes at least a transmission and reception device for directly communicating with the processing apparatus 3.

A configuration of the transmission and reception device is appropriately determined in accordance with a communication method with the processing apparatus 3.

For example, if the processing apparatus 3 is configured as a server apparatus over a network N, the communication module is configured to be connectable to the network N by using a wireless LAN (IEEE802.11, etc.) such as WiFi (Wireless Fidelity) or a 3G or 4G network for mobile communication.

Alternatively, the transmission and reception device can be connected to the processing apparatus 3 by using a short-distance wireless communication such as "Wi-Fi (registered trademark)", "Zigbee (registered trademark)", "Bluetooth (registered trademark)", "Bluetooth Low Energy", "ANT (registered trademark)", "ANT+ (registered trademark)", and "EnOcean (registered trademark)".

Furthermore, although not shown in the figure, the information processing system may be constituted of only the electronic apparatus without including the communication apparatus and the processing apparatus. That is, a control unit of the electronic apparatus 1 may be configured to generate information on a surrounding environment of the electronic apparatus on the basis of charge accumulation information and to output a control signal or the like based on that information. This control unit may be a control unit included in the communication module described above (see the reference sign 152 of FIG. 2) or may be constituted of a control module or the like including a CPU and the like, the control module being different from the above control unit. Further, in the latter case, the electronic apparatus may include a power supply apparatus for driving that control module.

Other Modified Example

For example, the information processing apparatus 100 may have a configuration not including a plurality of electronic apparatuses 1 but including only one electronic apparatus. With this, the control unit 31 can generate information on a surrounding environment of that electronic apparatus 1.

APPLICATION EXAMPLES

In the above description, the information processing system 100 has been described as a system introduced into the stockbreeding facility. The information processing system 100 may be applied as the following system, for example.

Application Example 1: Elderly-Person Support System

The information processing system 100 may be a support system for watching over elderly persons. For example, the information processing system 100 can be a system introduced into a nursing-care facility.

In this case, the electronic apparatus 1 is attached to an elderly person who reside in or goes to a nursing-care facility.

The communication apparatus 2 may be installed in, for example, a part of the nursing-care facility. Alternatively, the information processing system 100 may have a configuration including no communication apparatus as in Modified Example 2-7.

The processing apparatus 3 is constituted of an information processing apparatus or the like introduced into the nursing-care facility. The processing apparatus 3 can generate, on the basis of accumulation information output from each electronic apparatus 1, information on a living condition, a health state, and the like of an elderly person as surrounding environment information of the electronic apparatus 1. The processing apparatus 3 can transmit those pieces of generated information to a personal digital assistant of a family of the elderly person, staff of the facility, or the like registered in advance, to notify the family, the staff, or the like of the information.

If the processing apparatus 3 can acquire information on a position of the electronic apparatus 1 as in Modified Example 2-1 described above, the processing apparatus 3 can generate information on a position of the elderly person. With this, the staff of the nursing-care facility can easily search for the position of the elderly person, for example.

Further, the information processing system 100 can be a support system for watching over children, pupils, and students with disabilities, as in the elderly-person support system described above.

In this case, the electronic apparatus 1 is attached to a student or the like with disability.

The communication apparatus 2 may be installed in, for example, a part of a school facility to which the student or the like commutes. Alternatively, the information processing system 100 may have a configuration including no communication apparatus as in Modified Example 2-7.

The processing apparatus 3 can be an information processing apparatus or the like introduced into a school (special school) facility to which a student or the like with disability commutes or another facility to which the student goes. The processing apparatus 3 can generate, on the basis of accumulation information output from each electronic apparatus 1, information on a living condition, a health state, and the like of the student or the like with disability or information on a position, as surrounding environment information of the electronic apparatus 1. The processing apparatus 3 can transmit those pieces of generated information to a personal digital assistant of a parent or the like registered in advance, to notify the parent or the like of the information.

With this, the elderly facility, the school, and the like can grasp the living conditions and the health states of elderly persons, students, and the like and can also emphasize safety to the family of the person wearing the electronic apparatus 1.

Further, the person wearing the electronic apparatus 1 can live securely and safely.

Further, the family or parent of the person wearing the electronic apparatus 1 is notified of the information and can thus grasp the living condition, the health state, the position, and the like of the person who is wearing the electronic apparatus 1 and is in a distant place. The family or parent can live more securely.

Application Example 2: Pupil and Student Support System

The information processing system 100 can be a support system for watching over a school life.

In this case, the electronic apparatus 1 is attached to a pupil or the like.

The communication apparatus 2 may be installed in, for example, a part of a school facility to which the pupil or the like commutes. Alternatively, the information processing system 100 may have a configuration including no communication apparatus as in Modified Example 2-7.

The processing apparatus 3 can be an information processing apparatus or the like introduced into the school facility. The processing apparatus 3 can generate, on the basis of accumulation information output from each electronic apparatus 1, information on a living condition, a health state, or a position of the pupil or the like, as surrounding environment information of the electronic apparatus 1. Further, if time information can be acquired or generated together with the accumulation information as in Modified Example 2-2 described above, the processing apparatus 3 can also generate information on a time on the way to and from school of the pupil or the like. The processing apparatus 3 can transmit those pieces of generated information to a personal digital assistant of a parent or the like registered in advance, to notify the parent or the like of the information.

With this, the school facility can grasp the living conditions and the health states of pupils or the like and also manage the way to and from school. Further, the school facility can also emphasize safety with respect to mistreat or bullying to the parent.

Further, the pupil or the like who wears the electronic apparatus 1 can live securely and safely.

Further, the parent can also watch over the school life with peace of mind and can also cope with an abnormality quickly.

Application Example 3: Stray Child Search System

The information processing system 100 can be a stray child search system introduced into a commercial facility, a leisure facility, an event venue, or the like.

In this case, the electronic apparatus 1 is attached to a child who goes in a commercial facility, a leisure facility, an event venue, or the like.

The communication apparatus 2 may be installed in, for example, a predetermined site of the facility. Alternatively, the information processing system 100 may have a configuration including no communication apparatus as in Modified Example 2-7.

The processing apparatus 3 can be an information processing apparatus or the like introduced into the facility described above or the like. The processing apparatus 3 can generate, on the basis of accumulation information output from each electronic apparatus 1, information on behavior or a position of a child, as surrounding environment information of the electronic apparatus 1. The processing apparatus 2 can transmit those pieces of generated information to a personal digital assistant of a parent or the like registered in advance, to notify the parent or the like of the information.

Alternatively, the communication apparatus 2 may include a notification unit including a speaker, a vibrator, an LED lamp, or the like and may be configured to be portable by a person leading a child. In this case, for example, when a distance from the electronic apparatus 1 attached to the child is a predetermined distance or more, the communication apparatus 2 can notify the person of that information by using sound, vibration, indication, or the like of the notification unit.

With this, the person leading the child wearing the electronic apparatus 1 can easily search for the child even when the child is lost.

Further, the facility described above or the like can not only reduce the burden of operations on the stray child but also accurately grasp visitors by lending of the electronic apparatus 1 and the communication apparatus 2. This can be used as a reference for advertising strategies and customer collection. Further, the facility described above or the like can grasp the behavior of the child and the family of the child who are visitors. This can be used as a reference for improvement in traffic lines of visitors and sales strategies.

Application Example 4: Pet Management System

The information processing system 100 can be a pet management system.

In this case, the electronic apparatus 1 is attached to an animal kept as a pet.

The communication apparatus 2 may be installed in, for example, the house of the owner of the pet. Alternatively, the information processing system 100 may have a configuration including no communication apparatus as in Modified Example 2-7.

The processing apparatus 3 can be an information processing apparatus or the like of an animal hospital where the pet has an examination. The processing apparatus 3 can generate, on the basis of accumulation information output from each electronic apparatus 1, information on behavior or a position of the animal, as surrounding environment information of the electronic apparatus 1. The processing apparatus 2 can transmit those pieces of generated information to a personal digital assistant of the owner or the like registered in advance, to notify the owner or the like of the information.

With this, if losing the trace of the pet, the pet owner can easily search for the pet and can grasp a health state or an abnormality of the pet.

Further, the animal hospital can grasp daily behavior or a health state of the pet, to thus grasp a management state of the pet owner and give an accurate breeding instruction.

Application Example 5: Group Tour Smoothing System

The information processing system 100 can be a support system for smoothly carrying out a group tour.

In this case, the electronic apparatus 1 is attached to each of participants of a group tour.

The communication apparatus 2 may be installed in a vehicle (bus etc.) used for the group tour. Alternatively, the information processing system 100 may have a configuration including no communication apparatus as in Modified Example 2-7.

The processing apparatus 3 can be an information processing apparatus or the like carried by a tour guide, for example. The processing apparatus 3 can generate, on the basis of accumulation information output from each electronic apparatus 1, information on behavior or a position of the participant of the group tour, as surrounding environment information of the electronic apparatus 1. The processing apparatus 2 can transmit those pieces of generated information to a personal digital assistant of a family of the participant or the like registered in advance, to notify the family or the like of the information.

With this, the travel agent can grasp the behavior of the participants, to thus take measures suited to the occasion and also reduce a risk of an incident or accident that the participants or the like may meet. Further, the travel agent can utilize the acquired information in improvement of the services, for example.

Further, the participants of the group tour can enjoy the trip securely and safely.

Furthermore, the family or the like of the participant receives the information and can thus confirm the safety of the participant and grasp a change of an itinerary or the like.

Third Embodiment

An electronic apparatus 5 that is capable of outputting accumulation information in a different communication method will be described as a third embodiment. In the following description, configurations similar to those of the electronic apparatus 1 will be denoted by identical reference signs and detailed descriptions thereof will be omitted.

[Configuration of Electronic Apparatus]

Figure 18:
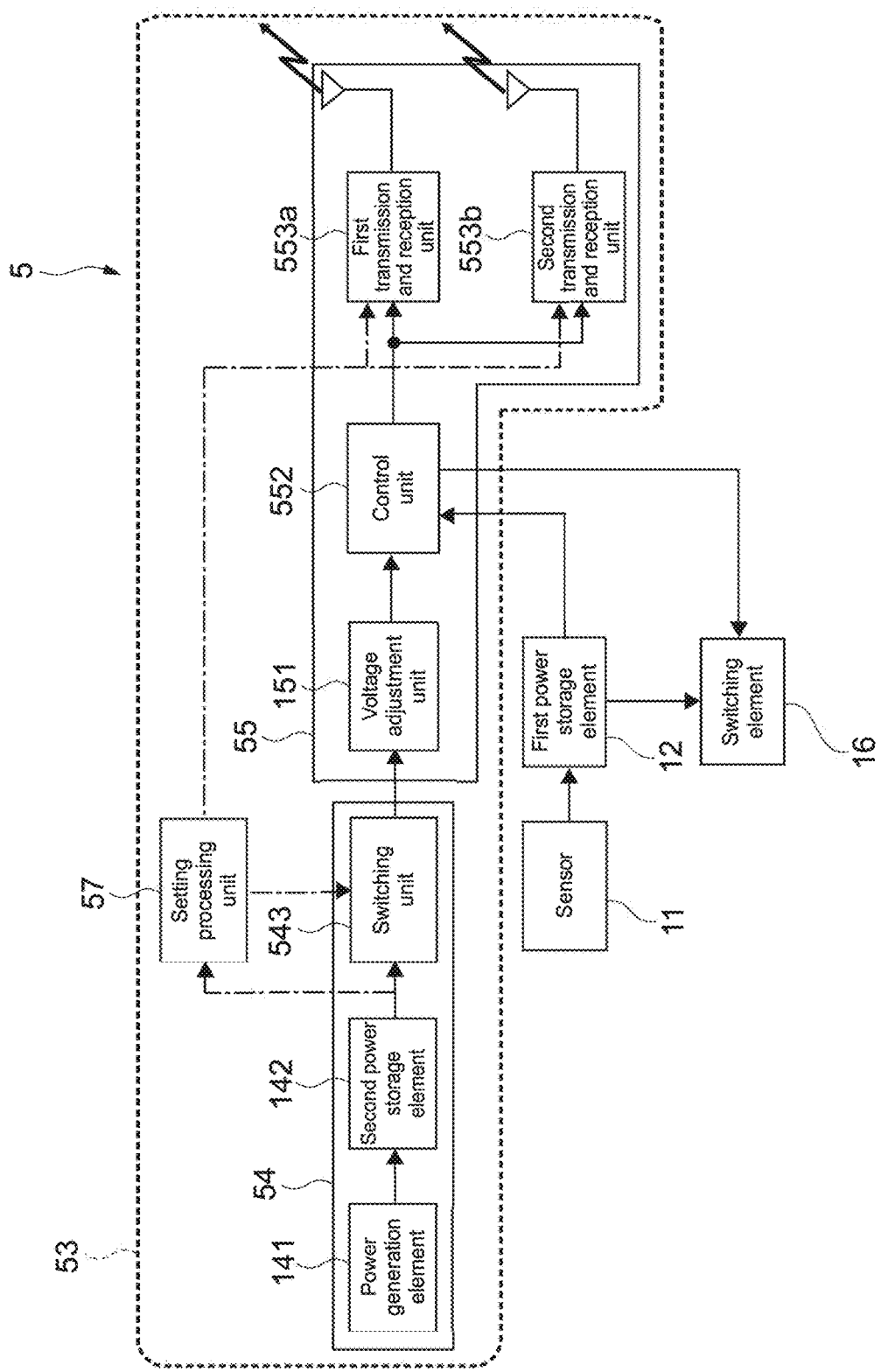
FIG. 18 is a block diagram showing a configuration of an electronic apparatus according to a third embodiment of the present technology.

FIG. 18 is a block diagram showing a configuration of the electronic apparatus 5 according to this embodiment.

The electronic apparatus 5 includes a sensor 11, a first power storage element (power storage element) 12, a switching element 16, and a communication module 53.

The communication module 53 includes an electric power supply unit 54, a communication processing unit 55, and a setting processing unit 57. Note that a power generation element 141 and a second power storage element 142 of the electric power supply unit 54, and a voltage adjustment unit 151 of the communication processing unit 55 can be configured as in the first embodiment.

When the amount of electric power generated with energy in a surrounding environment is a predetermined electric power amount or more, a switching unit 543 is switched from a blocking state in which supply of electric power to the communication processing unit 55 is blocked to a conduction state in which electric power is supplied to the communication processing unit 55.

In this embodiment, the switching unit 543 can apply a first electric power amount and a second electric power amount, as a predetermined electric power amount with which the switching unit is switched to the conduction state. Note that similarly to the switching unit 143, the switching unit 543 can use, for example, a voltage value or electric field value in the second power storage element 142, a charge amount accumulated in the second power storage element 142, or the like, as a determination reference of the electric power amount supplied from the electric power supply unit 14.

The communication processing unit 55 is configured to be capable of being switched between a stand-by state and an operating state on the basis of the electric power supplied from the electric power supply unit 54. In the operating state, the communication processing unit 55 is configured to be capable of acquiring charge accumulation information from the first power storage element 12 and outputting the accumulation information.

In this embodiment, in the operating state, the communication processing unit 55 is capable of outputting accumulation information under a first output condition and outputting accumulation information under a second output condition that is different from the first output condition. The "output condition" used herein includes conditions such as a communication method and a radio field intensity. If the communication processing unit 55 can perform communication using a plurality of communication methods, the output condition may include conditions of, for example, a type of the communication method and a combination thereof. Examples of the communication methods applicable by the communication processing unit 55 can include communication methods such as "Wi-Fi (registered trademark)", "Zigbee (registered trademark)", "Bluetooth (registered trademark)", "Bluetooth Low Energy", "ANT (registered trademark)", "ANT+ (registered trademark)", "EnOcean (registered trademark)", and NFC (Near Field Communication), communication methods utilizing radio waves and infrared rays other than the communication methods described above, communication methods utilizing an electric field, communication methods utilizing sound waves, and a 3G or 4G communication method.

The communication processing unit 55 includes a plurality of transmission and reception units 553*a* and 553*b*, each of which can output charge accumulation information of the first power storage element 12. Note that although FIG. 18 shows an example of the two transmission and reception units 553*a* and 553*b*, three or more transmission and reception units may be provided.

The first transmission and reception unit 553*a* is configured as, for example, a wireless module. The first transmission and reception units 553*a* may perform, for example, communication utilizing electromagnetic waves (including infrared rays) or communication utilizing an electric field. Examples of a specific method therefor can include a communication method utilizing a band of several hundreds MHz (megahertz) to several GHz (gigahertz), such as "Wi-Fi (registered trademark)", "Zigbee (registered trademark)", "Bluetooth (registered trademark)", "Bluetooth Low Energy", "ANT (registered trademark)", "ANT+ (registered trademark)", "EnOcean (registered trademark)", and an NFC (Near Field Communication). Note that the frequency band used for the communication is not limited to the above.

The second transmission and reception unit 553*b* is also configured as a wireless module similarly to the first transmission and reception unit 553*a*, and the communication methods exemplified above can be applied thereto. The second transmission and reception unit 553*b* typically applies a communication method different from that for the first transmission and reception unit 553*a*.

In the communication processing unit 55, under the first output condition, one or more of the transmission and reception units 553*a* and 553*b* operates or operate, and under the second output condition, one or more of the transmission and reception units 553*a* and 553*b*, which have a different combination from that under the first output condition, operates or operate. With this, a communication method having a different combination between the first output condition and the second output condition can be selected.

The setting processing unit 57 is configured to be capable of setting the output condition of the communication processing unit 55 to one of the first output condition and the second output condition. In this embodiment, the setting processing unit 57 selects one or more transmission and reception units to be operate, out of the plurality of transmission and reception units 553*a* and 553*b*, and can thus set the output condition of the communication processing unit 55.

Specifically, the setting processing unit 57 may include a processor such as an MPU and memories such as a ROM and a RAM. Note that a long dashed short dashed line shown in FIG. 18 represents an enable line on the setting processing unit 57.

The setting processing unit 57 is also configured to be capable of setting a predetermined electric power amount, with which the switching unit 543 is switched to the conduction state, to one of a first electric power amount corresponding to the first output condition and a second electric power amount corresponding to the second output condition, on the basis of a change amount of the electric power. With this, when setting the predetermined electric power amount to the first electric power amount, the setting processing unit 57 can set the output condition of the communication processing unit 55 to the first output condition, and when setting the predetermined electric power amount to the second electric power amount, the setting processing unit 57 can set the output condition of the communication processing unit 55 to the second output condition.

The setting processing unit 57 may detect, as a change amount of the electric power, a voltage value or electric field value in the second power storage element 142, a charge amount accumulated in the second power storage element 142, or the like, at the last output or after the elapse of a predetermined time from the activation of the electronic apparatus 5. In this case, when a voltage value of the second power storage element 142 after the elapse of a predetermined time is a predetermined threshold or more, the setting processing unit 57 can set the second electric power amount, and when the voltage value is less than the predetermined threshold, the setting processing unit 57 can set the first electric power amount. Alternatively, the setting processing unit 57 monitors the voltage value or the like of the second power storage element 142, and can thus set the electric power amount on the basis of a time derivative value of the voltage value of the second power storage element 142.

Similarly to the control unit 152, a control unit 552 acquires charge accumulation information from the first power storage element 12 in the operating state and also executes transmission control of the transmission and reception units 553*a* and 553*b*. Note that in this embodiment the setting processing unit 57 may perform transmission control of the transmission and reception units 553*a* and 553*b*. Alternatively, the control unit 552 may also function as the setting processing unit 57.

[Operation Example of Electronic Apparatus]

A typical operation example of the electronic apparatus 5 having the configuration described above will be described.

Figure 19:
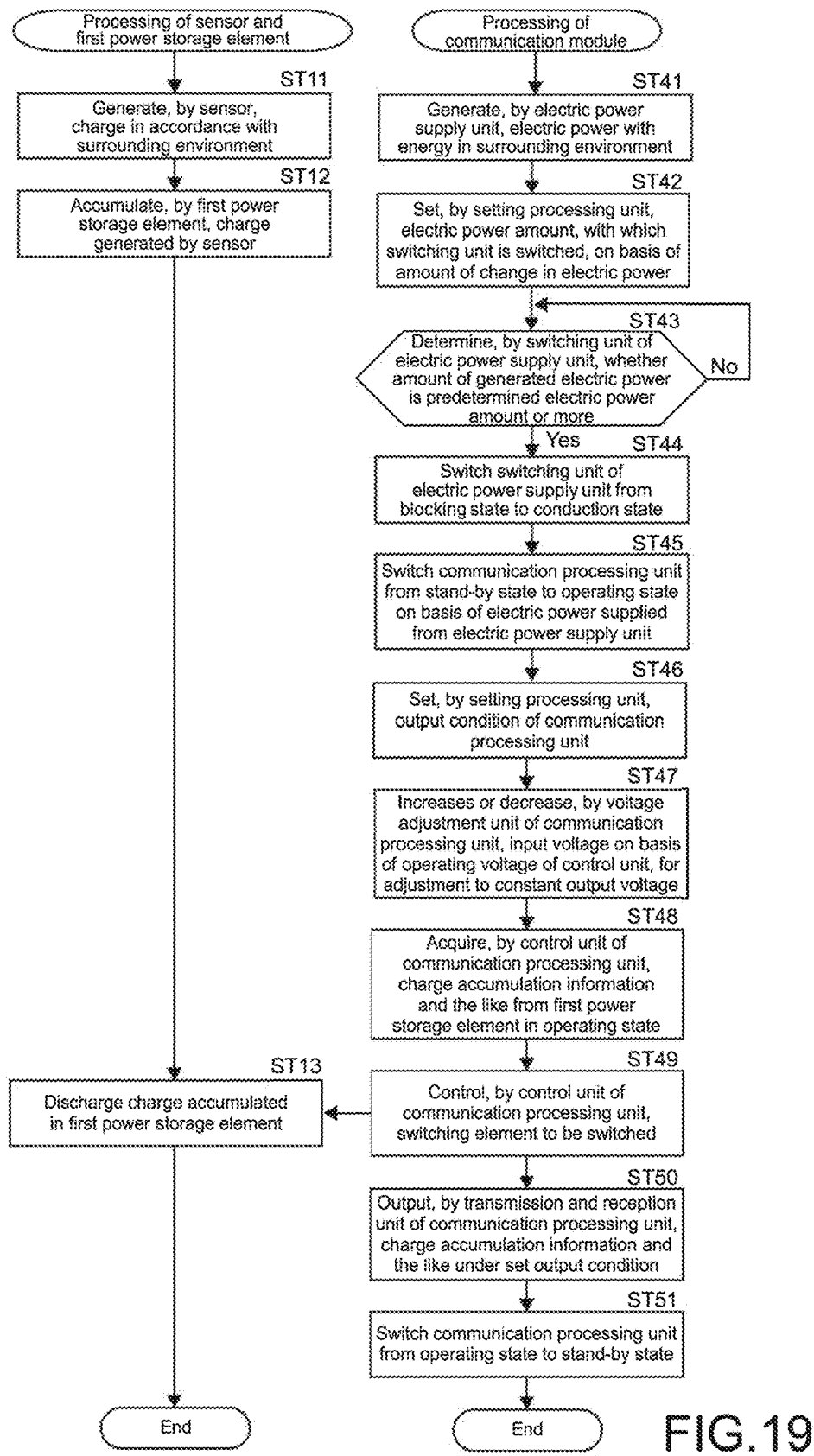

FIG. 19 is a flowchart describing an example of a flow of processing when the electronic apparatus 5 outputs accumulation information and the like. In the figure, ST11 to ST13 are executed by the sensor 11 and the first power storage element 12, and ST41 to ST51 are executed by the communication module 53. The processing of the sensor 11 and the first power storage element 12 are similar to the processing in the electronic apparatus 1 shown in FIG. 4. Note that here description will be given assuming that the sensor 11 is a vibration power generation element that generates charge in accordance with vibrations, and the power generation element 141 is an element capable of generating solar power.

Firstly, the sensor 11 generates charge in accordance with a surrounding environment (ST11).

For example, the sensor 11 vibrates in accordance with a motion of a user (including a human and an animal) to which the electronic apparatus 1 is attached. The sensor 11 generates charge.

Subsequently, the first power storage element 12 accumulates the charge generated by the sensor 11 (ST12).

Meanwhile, the electric power supply unit 14 of the communication module 53 generates electric power with energy in a surrounding environment (ST41).

Specifically, the power generation element 141 first generates electric power. For example, when a user wearing the electronic apparatus 1 goes outside in fine weather, the power generation element 141 is irradiated with solar light, and thus the power generation element 141 generates electric power.

Subsequently, the electric power generated by the power generation element 141 is accumulated as charge in the second power storage element 142 such as a capacitor. Also in this case, a voltage corresponding to the accumulation of the charge is generated in the second power storage element 142.

Subsequently, the setting processing unit 57 sets a predetermined electric power amount, with which the switching unit 543 is switched, to one of a first electric power amount corresponding to a first output condition and a second electric power amount corresponding to a second output condition, on the basis of a change amount of the electric power (ST43).

Figure 20:
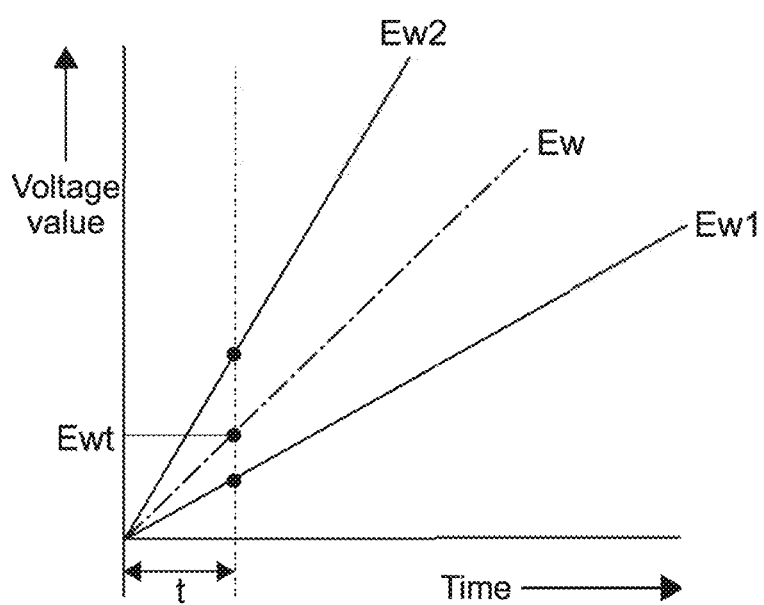
FIG. 20 is a graph describing setting processing for an electric power amount in the operation example described with reference to FIG. 19.

FIG. 20 is a graph describing the setting processing of the electric power amount in the setting processing unit 57, in which the horizontal axis represents a time, and the vertical axis represents a voltage value of the second power storage element 142. Further, in the graph, t represents a predetermined time in which the setting processing of the electric power amount is performed, Ewt represents a threshold of a voltage value used for setting the electric power amount, Ew1 indicated by a solid line represents an example of the transition of the voltage value of the second power storage element 142 when switched to the conduction state with the first electric power amount, and Ew2 represents the transition of the voltage value of the second power storage element 142 when switched to the conduction state with the second electric power amount. Further, Ew indicated by the long dashed short dashed line represents an example of the transition of the voltage value when the voltage value Ewt is obtained at a time t.

In this operation example, the setting processing unit 57 detects a voltage value in the second power storage element 142 at the time t, and determines whether that voltage value is Ewt or larger. If the voltage value is Ewt or larger, the setting processing unit 57 determines that the amount of change in voltage is large, and thus sets the reference voltage, with which the switching unit 543 is switched, to a voltage value corresponding to the second electric power amount. Meanwhile, if the voltage value is less than Ewt, the setting processing unit 57 determines that the amount of change in voltage is small, and thus sets the reference voltage, with which the switching unit 543 is switched, to a voltage value corresponding to the first electric power amount.

Subsequently, the switching unit 543 determines whether the amount of the electric power generated with energy in a surrounding environment is the set electric power amount or more (ST43).

If it is determined that the amount of the electric power is the set electric power amount or more (YES in ST43), the switching unit 543 is switched from the blocking state to the conduction state (ST44).

Note that the processing of ST43 and ST44 in this operation example depends on that the state of the switching unit 543 is switched when the voltage of the second power storage element 142 is the reference voltage or more. The determination processing of ST43 is not performed by a certain functional block.

Subsequently, the communication processing unit 55 of the communication module 53 is switched from the stand-by state to the operating state on the basis of the electric power supplied from the electric power supply unit 54 (ST45).

Specifically, the switching unit 543 is switched to the conduction state, and thus the electric power generated by the electric power supply unit 54 is supplied to the communication processing unit 55, and the communication processing unit 55 is switched to the operating state.

The setting processing unit 57 then sets the output condition of the communication processing unit 55 (ST46). In this operation example, when setting the first electric power amount, the setting processing unit 57 sets the output condition of the communication processing unit 55 to the first output condition, and when setting the second electric power amount, the setting processing unit 57 sets the output condition of the communication processing unit 55 to the second output condition.

In this operation example, it is assumed that the first transmission and reception unit 553*a* applies a communication method utilizing Bluetooth Low Energy in a frequency band of 2.4 GHz, and the second transmission and reception unit 553*b* applies a communication method utilizing radio waves in a band of 920 MHz.

For example, the communication processing unit 55 performs setting such that only the first transmission and reception unit 553*a* operates under the first output condition, and both of the first transmission and reception unit 553*a* and the second transmission and reception unit 553*b* operate under the second output condition.

Subsequently, the voltage adjustment unit 151 of the communication processing unit 55 increases or decreases an input voltage on the basis of an operating voltage of the control unit 552 so as to keep an output voltage constant (ST47).

Subsequently, the control unit 552 of the communication processing unit 55 acquires the charge accumulation information from the first power storage element 12 in the operating state, and also acquires identification information of the sensor 11, which is stored in the ROM or the like (ST48).

For example, the control unit 552 acquires, as charge accumulation information, information of a voltage value of the first power storage element 12 that is based on the accumulated charge.

Specifically, the control unit 552 reads a program stored in, for example, the ROM and executes processing corresponding to a code described in the program.

Subsequently, the control unit 552 controls the switching element 16 to be switched from the blocking state to the conduction state (ST49). With this, the first power storage element 12 discharges the accumulated charge (ST13).

Subsequently, the transmission and reception units 553*a* and 553*b* of the communication processing unit 55 output, under the set output condition, the acquired charge accumulation information and the identification information of the sensor (ST50). Specifically, the transmission and reception unit 553 selected in accordance with the output condition in ST46 outputs the information.

In the operation example, if the communication processing unit 55 is set to the first output condition, the transmission and reception unit 553a outputs the accumulation information and the like by using Bluetooth Low Energy, and if the communication processing unit 55 is set to the second output condition, the transmission and reception units 553a and 553b respectively output the accumulation information and the like by using two types of communication methods, Bluetooth Low Energy and a band of 920 MHz.

Lastly, because of consumption of the supplied electric power, the communication processing unit 55 is switched from the operating state to the stand-by state again (ST51). At that time, the control unit 552 may control the switching element 16 to be switched from the conduction state to the blocking state.

The electronic apparatus 5 repeats the processing, which includes the steps described above, as one cycle.

[Information Processing System Using Electronic Apparatus]

Figure 21:
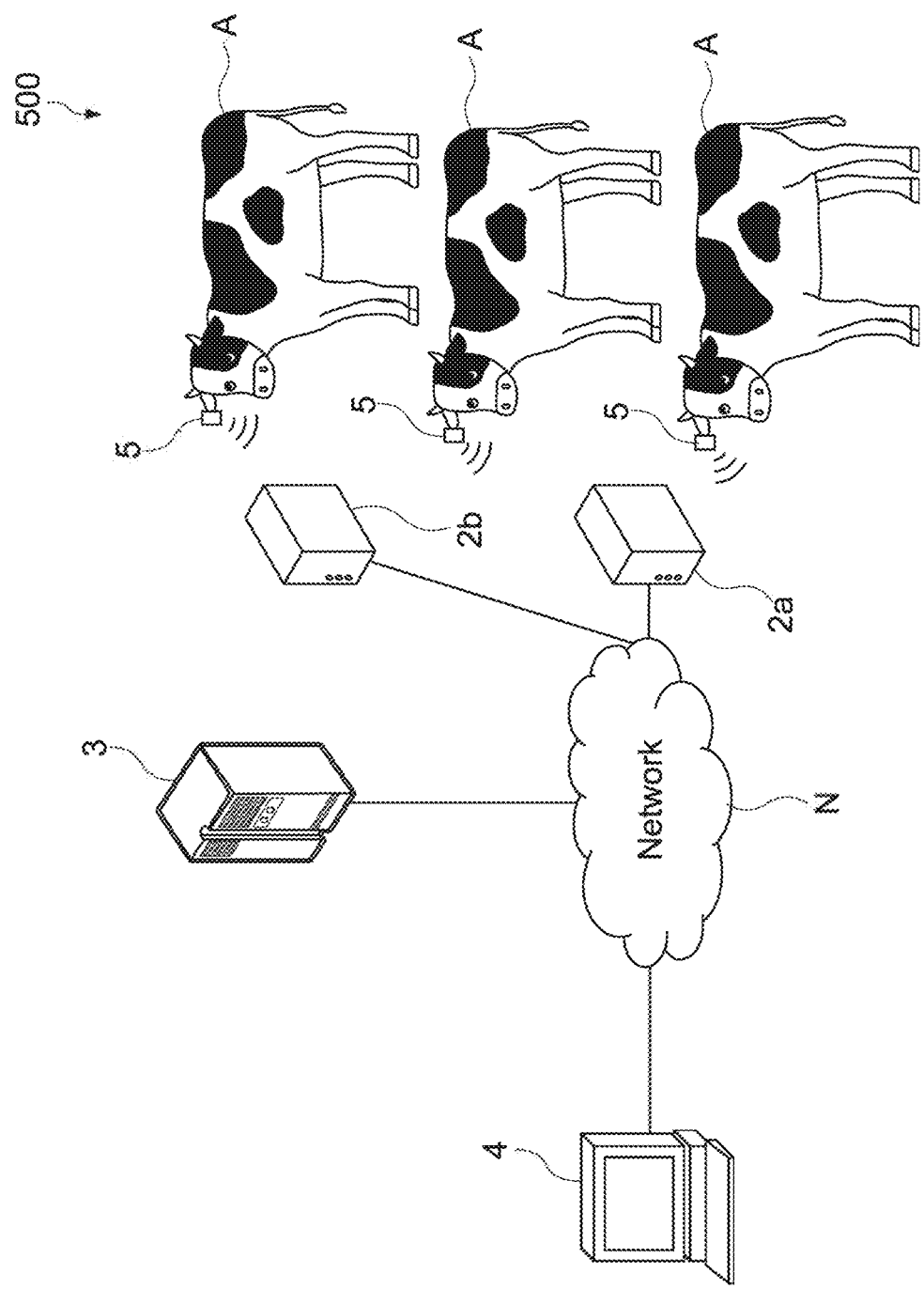
FIG. 21 is a schematic diagram showing a schematic configuration of an information processing system including the electronic apparatus.

The electronic apparatus 5 described above may be used in an information processing system as shown in FIG. 21.

As shown in the figure, an information processing system 500 includes a plurality of electronic apparatuses 5, a plurality of communication apparatuses 2a and 2, and a processing apparatus 3. The communication apparatuses 2a and 2b and the processing apparatus 3 can apply a configuration similar to that of the information processing system 100 in the second embodiment, and thus detailed descriptions thereof will be omitted.

For example, the information processing system 500 is also a system introduced into, for example, a stockbreeding facility. The processing apparatus 3 is configured to be capable of acquiring predetermined information from the electronic apparatus 5 attached to each livestock animal A and generating information on a surrounding environment of the electronic apparatus 5.

The communication apparatuses 2a and 2b receive information output from the electronic apparatus 5 and transmits the received information to the processing apparatus 3 on a network N.

The communication apparatuses 2a and 2b may be capable of performing communication by different communication methods, respectively. As one example, the communication apparatus 2a is installed indoors and is capable of performing communication by Bluetooth Low Energy in a frequency band of 2.4 GHz. Further, the communication apparatus 2b is installed outdoors and is capable of performing communication utilizing radio waves in a band of 920 MHz. In such a manner, even when the communication apparatuses 2a and 2b have different communication methods, the communication between those apparatuses is available as long as the electronic apparatus 5 is set to a condition in which simultaneous output by a plurality of communication methods is available.

Alternatively, each of the communication apparatuses 2a and 2b may be capable of performing communication by a plurality of communication methods or may be capable of performing communication by a single communication method.

The electronic apparatus 5 of this embodiment can apply a plurality of output conditions in which the communication methods and the like are different. Depending on the output conditions, a communication distance, the straight traveling property of radio waves, power consumption, and the like differ. In this embodiment, the information processing system 500 utilizing such differences in the output conditions can be established.

Here, the following points can be given as advantages of applying a plurality of output conditions.

The first point is, as described above, that the communication with the electronic apparatus 5 is available if the communication apparatuses 2a and 2b have different communication methods.

For example, if the communication apparatuses 2a and 2b having different communication methods are installed at random positions, the electronic apparatus 5 can communicate with any of the communication apparatuses 2a and 2b.

Alternatively, if the communication apparatuses 2a and 2b having different communication methods are respectively installed outdoors and indoors, the electronic apparatus 5 can also set an output condition corresponding to each of the communication methods of the communication apparatuses 2a and 2b outdoors or indoors. In this case, if the power generation element 141 of the electronic apparatus 5 is a solar power generation element, a power generation amount can differ between outdoors and indoors. Further, it is also possible to select a suitable output condition in accordance with a power generation environment, e.g., an output condition set for outdoors is a communication method in which power consumption is large and a communication distance is long, and an output condition set for indoors is a communication method in which power consumption is small and a communication distance is short.

The second point is, as described above, that when a correlation between the signal strength of communication data and a communication distance is used to generate information on a relative position of the electronic apparatus 5 from the communication apparatus 2, its accuracy and convenience can be enhanced.

For example, when the distance of the electronic apparatus 5 from the communication apparatus 2 is calculated, use of the signal strengths by two different types of communication methods can enhance calculation accuracy of the distance. In this case, it is assumed that one communication apparatus 2 can perform reception by a plurality of communication methods, and the electronic apparatus 5 can also be set to an output condition using the identical combination of communication methods. With this, if the distance between the electronic apparatus 5 and the communication apparatus 2 is calculated using the radio field intensity of a signal output by each of the communication methods, the distance can be calculated at higher accuracy than using the radio field intensity by one type of communication method.

Further, if the distance between each of two or more communication apparatuses 2 and the electronic apparatus 5 is calculated, a relative position of the electronic apparatus 5 with respect to the two or more communication apparatuses 2 can be calculated in terms of triangulation. Also in this case, if the electronic apparatus 5 is set to an output condition using a plurality of communication methods, the relative position with respect to the communication apparatuses 2 using different communication methods can be calculated, and the relative position of the electronic apparatus 5 can be determined.

The third point is that information on an environment between the electronic apparatus 5 and the communication apparatus 2 can be generated utilizing a phenomenon in which the output conditions cause differences. As described above, depending on the communication methods and the like, a communication distance, the straight traveling property of radio waves, power consumption, and the like differ.

For example, using a difference in communication distance, the distance between each of the communication apparatuses 2 using different communication methods and the electronic apparatus 5 can be roughly estimates. Alternatively, using a difference in straight traveling property of radio waves, the presence/absence of an obstacle between the communication apparatus 2 and the electronic apparatus 5, and the like can be detected.

Furthermore, the electronic apparatus 5 of this embodiment can switch the output condition without performing complicated determination processing by a logic circuit or the like, and thus power consumption related to switching of the output condition can be suppressed. Therefore, a configuration capable of switching the output condition and having low power consumption can be realized.

Hereinabove, although the embodiments of the present technology have been described, the present technology is not limited to the embodiments described above and can be variously modified without departing from the gist of the present technology as a matter of course.

For example, the electronic apparatus can have configurations as shown in FIGS. 22 to 35.

Figure 22:
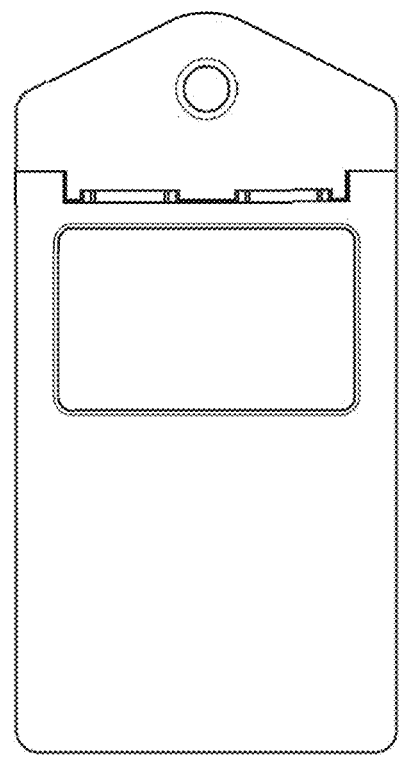
FIG. 22 is a front view showing a mode in which a tab is disposed at a reference position with respect to a main body in one example of the outer appearance of the electronic apparatus.
Figure 23:
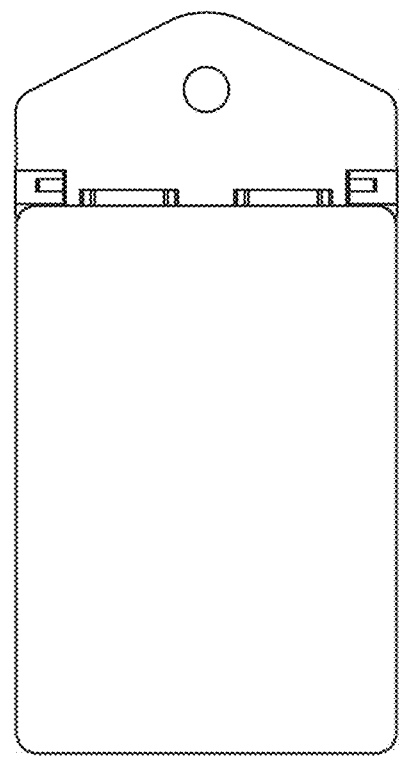
FIG. 23 is a rear view showing a mode in which the tab is disposed at the reference position with respect to the main body in one example of the outer appearance of the electronic apparatus.
Figure 24:
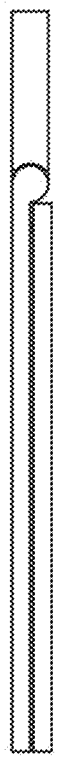
FIG. 24 is a right side view showing a mode in which the tab is disposed at the reference position with respect to the main body in one example of the outer appearance of the electronic apparatus.
Figure 25:
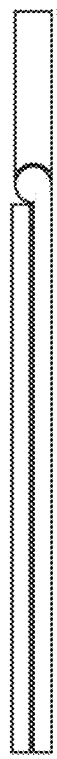
FIG. 25 is a left side view showing a mode in which the tab is disposed at the reference position with respect to the main body in one example of the outer appearance of the electronic apparatus.
Figure 26:
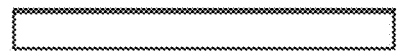
FIG. 26 is a plan view showing a mode in which the tab is disposed at the reference position with respect to the main body in one example of the outer appearance of the electronic apparatus.
Figure 27:
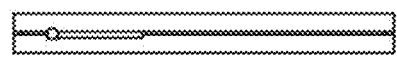
FIG. 27 is a bottom view showing a mode in which the tab is disposed at the reference position with respect to the main body in one example of the outer appearance of the electronic apparatus.
Figure 28:
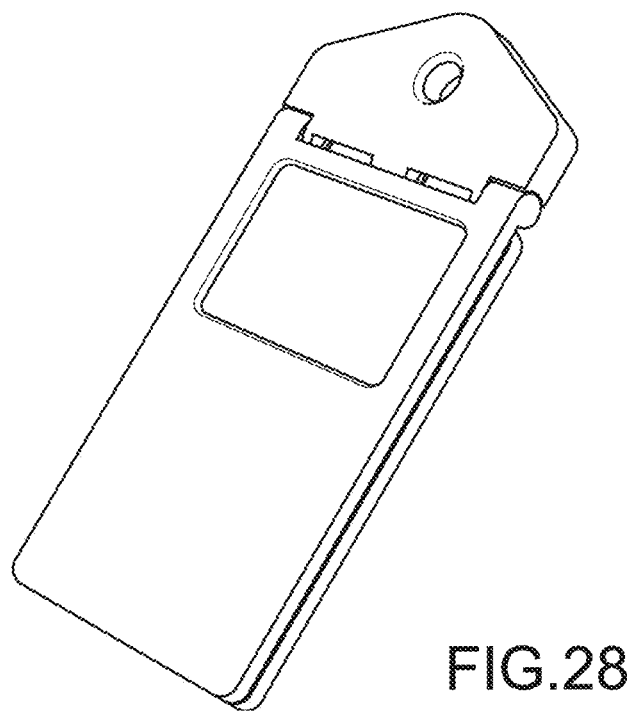
FIG. 28 is a perspective view showing a mode in which the tab is disposed at the reference position with respect to the main body in one example of the outer appearance of the electronic apparatus.

FIGS. 22 to 28 show modes in which the tab is disposed at a reference position with respect to the main body. FIG. 22 is a front view, FIG. 23 is a rear view, FIG. 24 is a right side view, FIG. 25 is a left side view, FIG. 26 is a plan view, FIG. 27 is a bottom view, and FIG. 28 is a perspective view.

Figure 29:
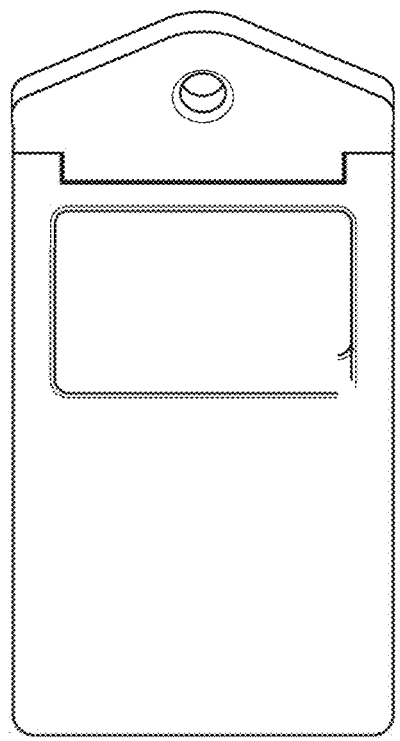
FIG. 29 is a front view showing a mode in which the tab is rotated by a predetermined angle from the reference position with respect to the main body in one example of the outer appearance of the electronic apparatus.
Figure 30:
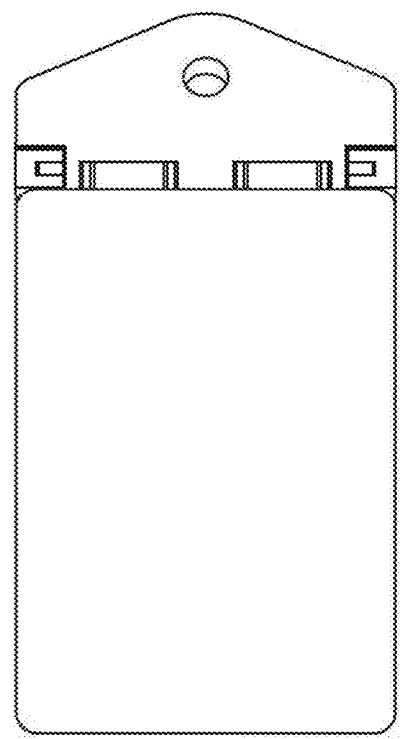
FIG. 30 is a rear view showing a mode in which the tab is rotated by a predetermined angle from the reference position with respect to the main body in one example of the outer appearance of the electronic apparatus.
Figure 31:
FIG. 31 is a right side view showing a mode in which the tab is rotated by a predetermined angle from the reference position with respect to the main body in one example of the outer appearance of the electronic apparatus.
Figure 32:
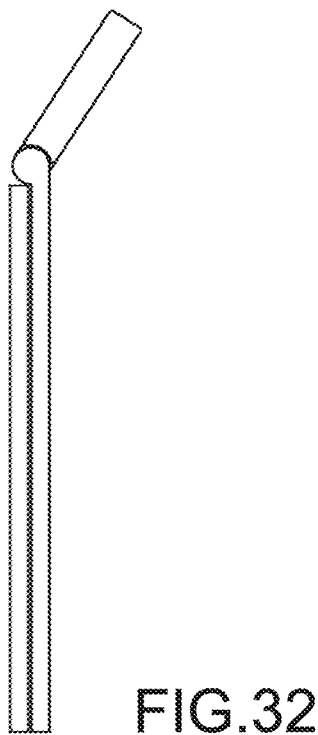
FIG. 32 is a left side view showing a mode in which the tab is rotated by a predetermined angle from the reference position with respect to the main body in one example of the outer appearance of the electronic apparatus.
Figure 33:
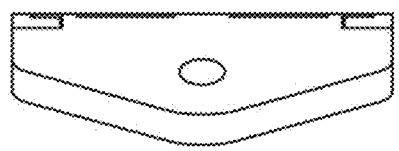
FIG. 33 is a plan view showing a mode in which the tab is rotated by a predetermined angle from the reference position with respect to the main body in one example of the outer appearance of the electronic apparatus.
Figure 34:
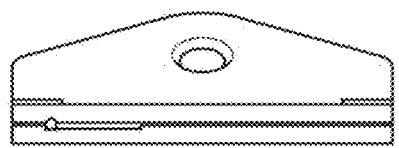
FIG. 34 is a bottom view showing a mode in which the tab is rotated by a predetermined angle from the reference position with respect to the main body in one example of the outer appearance of the electronic apparatus.
Figure 35:
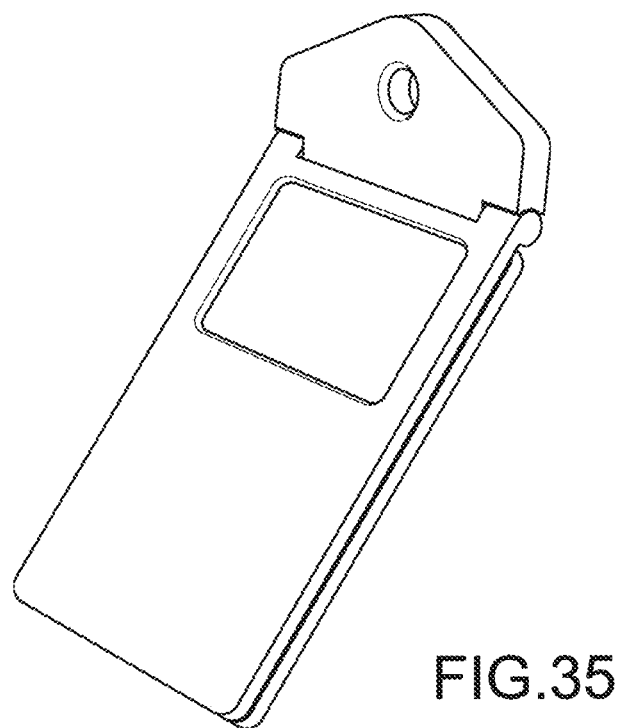
FIG. 35 is a perspective view showing a mode in which the tab is rotated by a predetermined angle from the reference position with respect to the main body in one example of the outer appearance of the electronic apparatus.

FIGS. 29 to 35 shows modes in which the tab is rotated by a predetermined angle from the reference position with respect to the main body. FIG. 29 is a front view, FIG. 30 is a rear view, FIG. 31 is a right side view, FIG. 32 is a left side view, FIG. 33 is a plan view, FIG. 34 is a bottom view, and FIG. 35 is a perspective view.

Note that the present technology can have the following configurations.

(1) An electronic apparatus, including:
  a sensor that generates charge in accordance with a surrounding environment;
  a power storage element that accumulates the generated charge; and
  a communication module that includes
    an electric power supply unit that supplies electric power by generating electric power with energy in a surrounding environment, and
    a communication processing unit that is configured to be capable of being switched between a stand-by state and an operating state on the basis of the electric power supplied from the electric power supply unit and is capable of acquiring accumulation information of the charge from the power storage element and outputting the accumulation information in the operating state.
(2) The electronic apparatus according to (1), in which
  the communication processing unit is switched, when the electric power is supplied from the electric power supply unit, from the stand-by state to the operating state, and consumes the supplied electric power in the operating state, to be switched from the operating state to the stand-by state.
(3) The electronic apparatus according to (2), in which
  the electric power supply unit further includes a switching unit that is switched, when the amount of the electric power generated with the energy in the surrounding environment is the predetermined electric power amount or more, from a blocking state in which supply of the electric power to the communication processing unit is blocked to a conduction state in which the electric power is supplied to the communication processing unit, and
  the communication processing unit is provided with the electric power by switching of the switching unit from the blocking state to the conduction state, and is switched from the stand-by state to the operating state.
(4) The electronic apparatus according to any one of (1) to (3), further including
  a switching element that is connected to the power storage element and is controlled, by the communication processing unit, to discharge the charge accumulated in the power storage element after the accumulation information of the charge is acquired by the communication processing unit.
(5) The electronic apparatus according to any one of (1) to (4), in which
  the communication processing unit outputs identification information of the sensor associated with the accumulation information of the charge in the operating state.
(6) The electronic apparatus according to any one of (1) to (5), in which
  the sensor generates charge in accordance with vibrations.
(7) The electronic apparatus according to any one of (1) to (5), in which
  the sensor generates charge in accordance with a temperature difference.
(8) The electronic apparatus according to any one of (1) to (5), in which
  the sensor generates charge in accordance with a light irradiation.
(9) The electronic apparatus according to any one of (1) to (5), in which
  the sensor generates charge by a near or far electromagnetic field of the sensor.
(10) The electronic apparatus according to any one of (1) to (5), in which
  the sensor generates charge in accordance with energy generated by an ion concentration difference.
(11) The electronic apparatus according to any one of (1) to (5), in which
  the sensor generates charge in accordance with energy generated by a chemical reaction.
(12) The electronic apparatus according to any one of (1) to (11), in which
  the accumulation information of the charge includes information of a voltage value of the power storage element, the voltage value being based on the accumulated charge.
(13) The electronic apparatus according to (12), in which the power storage element is a capacitor.
(14) The electronic apparatus according to any one of (1) to (13), which is configured to be attachable to a living body or configured to be attachable to a non-living body.
(15) The electronic apparatus according to any one of (1) to (14), further including
  a plurality of sensors that each generate charge in accordance with a surrounding environment; and
  a plurality of power storage elements that are respectively connected to the plurality of sensors and respectively accumulate charge generated in the plurality of sensors, in which
  the communication processing unit is configured to be capable of acquiring accumulation information of the charge from each of the plurality of power storage elements and outputting the acquired pieces of accumulation information in the operating state.
(16) The electronic apparatus according to (15), in which
  the communication processing unit outputs identification information of each of the plurality of sensors in the operating state, and
  the identification information of each of the plurality of sensors is associated with the accumulation information of the charge, the accumulation information being acquired from the power storage element connected to the sensor identified by the identification information.

(17) The electronic apparatus according to (3), in which the communication processing unit is capable of outputting the accumulation information under a first output condition and outputting the accumulation information under a second output condition different from the first output condition in the operating state, the communication module further includes a setting processing unit that is capable of setting an output condition of the communication processing unit to one of the first output condition and the second output condition, and the setting processing unit is capable of setting the predetermined electric power amount, with which the switching unit is switched to the conduction state, to one of a first electric power amount corresponding to the first output condition and a second electric power amount corresponding to the second output condition on the basis of a change amount of the electric power, the setting processing unit setting the output condition of the communication processing unit to the first output condition when setting the predetermined electric power amount to the first electric power amount, the setting processing unit setting the output condition of the communication processing unit to the second output condition when setting the predetermined electric power amount to the second electric power amount.

(18) The electronic apparatus according to (17), in which the communication processing unit further includes a plurality of transmission and reception units that are each capable of outputting the accumulation information, one or more of the plurality of transmission and reception units operate under the first output condition, one or more of the plurality of transmission and reception units, which have a different combination from that under the first output condition, operate under the second output condition, and the setting processing unit selects one or more of the plurality of transmission and reception units to be operated, to set the output condition of the communication processing unit.

(19) An information processing method for an electronic apparatus, the information processing method including:

generating, by a sensor, charge in accordance with a surrounding environment;

accumulating, by a power storage element, the generated charge;

supplying, by an electric power supply unit of a communication module, electric power by generating electric power with energy in a surrounding environment;

switching a communication processing unit of the communication module between a stand-by state and an operating state on the basis of the electric power supplied from the electric power supply unit;

acquiring, by the communication processing unit, accumulation information of the charge from the power storage element and outputting the accumulation information in the operating state.

(20) An information processing system, including:

an electronic apparatus including
a sensor that generates charge in accordance with a surrounding environment,
a power storage element that accumulates the generated charge, and
a communication module that includes
an electric power supply unit that supplies electric power by generating electric power with energy in a surrounding environment, and
a communication processing unit that is configured to be capable of being switched between a stand-by state and an operating state on the basis of the electric power supplied from the electric power supply unit and is capable of acquiring accumulation information of the charge from the power storage element and outputting the accumulation information in the operating state; and a processing apparatus that generates information on a surrounding environment of the electronic apparatus on the basis of the output accumulation information.

REFERENCE SIGNS LIST 1, 1A, 1B, 1C, 1D, 1E, 5 electronic apparatus
11, 111, 112, 11D, 11E sensor
12 first power storage element (power storage element)
13, 13A, 13B, 13C, 53 communication module
14, 14C, 54 electric power supply unit
15, 15A, 15B, 15C, 55 communication processing unit
100, 100A, 500 information processing system

The invention claimed is:

1. An electronic apparatus, comprising:
a sensor that generates charge in accordance with a surrounding environment;
a power storage element that accumulates the generated charge; and
a communication module that includes:
an electric power supply unit that supplies electric power by generating electric power with energy in a surrounding environment, and
a communication processing unit that is configured to be capable of being switched between a stand-by state and an operating state on the basis of the electric power supplied from the electric power supply unit and is capable of acquiring accumulation information of the charge from the power storage element and outputting the accumulation information in the operating state.

2. The electronic apparatus according to claim 1, wherein the communication processing unit is switched, when the electric power is supplied from the electric power supply unit, from the stand-by state to the operating state, and consumes the supplied electric power in the operating state, to be switched from the operating state to the stand-by state.

3. The electronic apparatus according to claim 2, wherein the electric power supply unit further includes a switching unit that is switched, when an amount of the electric power generated with the energy in the surrounding environment is a specific electric power amount or more, from a blocking state in which supply of the electric power to the communication processing unit is blocked to a conduction state in which the electric power is supplied to the communication processing unit, and the communication processing unit is provided with the electric power by switching of the switching unit from the blocking state to the conduction state, and is switched from the stand-by state to the operating state.

4. The electronic apparatus according to claim 3, wherein the communication processing unit is capable of: outputting the accumulation information under a first output condition and outputting the accumulation information under a second output condition different from the first output condition in the operating state, the communication module further includes a setting processing unit that is capable of setting an output condition of the communication processing unit to one of the first output condition and the second output condition, the setting processing unit is capable of setting the specific electric power amount, with which the switching unit is switched to the conduction state, to one of a first electric power amount corresponding to the first output condition and a second electric power amount corresponding to the second output condition on the basis of a change amount of the electric power, the setting processing unit setting the output condition of the communication processing unit to the first output condition when setting the specific electric power amount to the first electric power amount, and the setting processing unit setting the output condition of the communication processing unit to the second output condition when setting the specific electric power amount to the second electric power amount.

5. The electronic apparatus according to claim 4, wherein the communication processing unit further includes a plurality of transmission and reception units that are each capable of outputting the accumulation information, one or more of the plurality of transmission and reception units operate under the first output condition, one or more of the plurality of transmission and reception units, which have a different combination from that under the first output condition, operate under the second output condition, and the setting processing unit selects one or more of the plurality of transmission and reception units to be operated, to set the output condition of the communication processing unit.

6. The electronic apparatus according to claim 1, further comprising a switching element that is connected to the power storage element and is controlled, by the communication processing unit, to discharge the charge accumulated in the power storage element after the accumulation information of the charge is acquired by the communication processing unit.

7. The electronic apparatus according to claim 1, wherein the communication processing unit outputs identification information of the sensor associated with the accumulation information of the charge in the operating state.

8. The electronic apparatus according to claim 1, wherein the sensor generates charge in accordance with vibrations.

9. The electronic apparatus according to claim 1, wherein the sensor generates charge in accordance with a temperature difference.

10. The electronic apparatus according to claim 1, wherein the sensor generates charge in accordance with a light irradiation.

11. The electronic apparatus according to claim 1, wherein the sensor generates charge by a near or far electromagnetic field of the sensor.

12. The electronic apparatus according to claim 1, wherein the sensor generates charge in accordance with energy generated by an ion concentration difference.

13. The electronic apparatus according to claim 1, wherein the sensor generates charge in accordance with energy generated by a chemical reaction.

14. The electronic apparatus according to claim 1, wherein the accumulation information of the charge includes information of a voltage value of the power storage element, the voltage value being based on the accumulated charge.

15. The electronic apparatus according to claim 14, wherein the power storage element is a capacitor.

16. The electronic apparatus according to claim 1, which is configured to be attachable to a living body or configured to be attachable to a non-living body.

17. The electronic apparatus according to claim 1, further comprising:

a plurality of sensors that each generate charge in accordance with a surrounding environment; and a plurality of power storage elements that are respectively connected to the plurality of sensors and respectively accumulate charge generated in the plurality of sensors, wherein the communication processing unit is configured to be capable of: acquiring accumulation information of the charge from each of the plurality of power storage elements, and outputting the acquired accumulation information in the operating state.

18. The electronic apparatus according to claim 17, wherein the communication processing unit outputs identification information of each of the plurality of sensors in the operating state, the identification information of each of the plurality of sensors is associated with the accumulation information of the charge, and the accumulation information being acquired from the power storage element connected to the sensor identified by the identification information.

19. An information processing method for an electronic apparatus, the information processing method comprising:

generating, by a sensor, charge in accordance with a surrounding environment;

accumulating, by a power storage element, the generated charge;

supplying, by an electric power supply unit of a communication module, electric power by generating electric power with energy in a surrounding environment;

switching a communication processing unit of the communication module between a stand-by state and an operating state on the basis of the electric power supplied from the electric power supply unit; and acquiring, by the communication processing unit, accumulation information of the charge from the power storage element and outputting the accumulation information in the operating state.

20. An information processing system, comprising:

an electronic apparatus including a sensor that generates charge in accordance with a surrounding environment, a power storage element that accumulates the generated charge, and a communication module that includes an electric power supply unit that supplies electric power by generating electric power with energy in a surrounding environment, and a communication processing unit that is configured to be capable of being switched between a stand-by state and an operating state on the basis of the electric power supplied from the electric power supply unit and is capable of acquiring accumulation information of the charge from the power storage element and outputting the accumulation information in the operating state; and a processing apparatus that generates information on a surrounding environment of the electronic apparatus on the basis of the output accumulation information.

\* \* \* \* \*